(12) United States Patent
Wang et al.

(10) Patent No.: US 10,329,243 B2
(45) Date of Patent: Jun. 25, 2019

(54) BIPHENYL DERIVATIVE AND USES THEREOF

(71) Applicant: XI'AN LIBANG PHARMACEUTICAL CO., LTD, Xi'an, Shaanxi (CN)

(72) Inventors: Rutao Wang, Shaanxi (CN); Tao Chen, Shaanxi (CN); Long An, Shaanxi (CN); Yi Zhao, Shaanxi (CN); Weijiao Wang, Shaanxi (CN); Shupan Guo, Shaanxi (CN); Sa Xiao, Shaanxi (CN); Jinghua Pang, Shaanxi (CN); Huijing Hu, Shaanxi (CN)

(73) Assignee: XI'AN LIBANG PHARMACEUTICAL CO., LTD, Xi'an, Shaanxi (CN)

( * ) Notice: Subject to any disclaimer, the term of this patent is extended or adjusted under 35 U.S.C. 154(b) by 0 days.

(21) Appl. No.: 15/543,454

(22) PCT Filed: Mar. 11, 2016

(86) PCT No.: PCT/CN2016/076124
§ 371 (c)(1),
(2) Date: Jul. 13, 2017

(87) PCT Pub. No.: WO2016/112875
PCT Pub. Date: Jul. 21, 2016

(65) Prior Publication Data
US 2018/0141895 A1    May 24, 2018

(30) Foreign Application Priority Data
Jan. 13, 2015  (CN) .......................... 2015 1 0016733

(51) Int. Cl.
| | | |
|---|---|---|
| *C07C 229/08* | (2006.01) | |
| *A61K 31/05* | (2006.01) | |
| *A61K 31/192* | (2006.01) | |
| *A61K 31/222* | (2006.01) | |
| *A61K 31/223* | (2006.01) | |
| *C07C 65/105* | (2006.01) | |
| *C07C 69/16* | (2006.01) | |
| *C07C 69/40* | (2006.01) | |
| *C07C 39/15* | (2006.01) | |
| *A61P 25/28* | (2006.01) | |
| *C07C 69/08* | (2006.01) | |
| *C07C 39/367* | (2006.01) | |
| *C07C 25/18* | (2006.01) | |
| *C07F 9/09* | (2006.01) | |
| *C07C 271/42* | (2006.01) | |

(52) U.S. Cl.
CPC ............ *C07C 229/08* (2013.01); *A61K 31/05* (2013.01); *A61K 31/192* (2013.01); *A61K 31/222* (2013.01); *A61K 31/223* (2013.01); *A61P 25/28* (2018.01); *C07C 25/18* (2013.01); *C07C 39/15* (2013.01); *C07C 39/367* (2013.01); *C07C 65/105* (2013.01); *C07C 69/08* (2013.01); *C07C 69/16* (2013.01); *C07C 69/40* (2013.01); *C07C 271/42* (2013.01); *C07F 9/091* (2013.01)

(58) Field of Classification Search
CPC ..... C07C 229/08; C07C 39/15; C07C 65/105; C07C 69/16; C07C 69/40; A61P 25/28; A61K 31/05; A61K 31/192; A61K 31/222; A61K 31/223
See application file for complete search history.

(56) References Cited

U.S. PATENT DOCUMENTS

| | | | | |
|---|---|---|---|---|
| 2,785,188 A | * | 3/1957 | Coe .................. | C07C 46/08 252/404 |
| 4,100,204 A | * | 7/1978 | Rutledge ................ | C07C 37/11 552/291 |
| 4,386,174 A | | 5/1983 | Cogswell et al. | |
| 4,438,236 A | | 3/1984 | Cogswell et al. | |
| 6,087,513 A | * | 7/2000 | Liao .................... | C07D 301/19 549/214 |
| 9,693,963 B2 | * | 7/2017 | Wang ................... | A61K 31/05 |
| 2004/0191602 A1 | | 9/2004 | Ishikawa et al. | |
| 2007/0161702 A1 | | 7/2007 | Yokoyama et al. | |
| 2011/0052650 A1 | | 3/2011 | Morris et al. | |
| 2012/0121711 A1 | * | 5/2012 | Hu ...................... | A61K 9/5153 424/489 |
| 2013/0280330 A9 | * | 10/2013 | Hu ...................... | A61K 9/5153 424/489 |

(Continued)

FOREIGN PATENT DOCUMENTS

| | | |
|---|---|---|
| CN | 1630676 A | 6/2005 |
| CN | 101006094 A | 7/2007 |

(Continued)

OTHER PUBLICATIONS

CAS Abstract, JP 2000247920 (2000) (Year: 2000).*

(Continued)

*Primary Examiner* — Alexander R Pagano
(74) *Attorney, Agent, or Firm* — Hoffman Warnick LLC

(57) ABSTRACT

The present invention relates to a biphenyl derivative and use thereof, and the biphenyl derivative has a structure represented by the formula (I) as defined in the specification. The use refers the use of the biphenyl derivative or a pharmaceutically acceptable salt or solvate thereof, or a pharmaceutical composition comprising the biphenyl derivative or a pharmaceutically acceptable salt or solvate thereof in the preparation of a medicament for the treatment and/or prevention of ischemic stroke.

12 Claims, No Drawings

(56) References Cited

U.S. PATENT DOCUMENTS

| | | | | |
|---|---|---|---|---|
| 2014/0370101 A1* | 12/2014 | Wang | ...................... | A61K 31/05 424/489 |
| 2015/0352052 A1* | 12/2015 | Wang | ...................... | A61K 31/05 424/451 |
| 2015/0376099 A1* | 12/2015 | Wang | ...................... | C07C 39/15 568/730 |
| 2016/0235684 A1* | 8/2016 | Wang | ...................... | A61K 31/05 |
| 2018/0185299 A1* | 7/2018 | Wang | ...................... | A61K 9/08 |

FOREIGN PATENT DOCUMENTS

| | | | | |
|---|---|---|---|---|
| CN | 104546809 A | | 4/2015 | |
| CN | 104557532 A | | 4/2015 | |
| JP | 07089898 A | * | 4/1995 | |
| JP | H0789898 A | | 4/1995 | |
| JP | 2000247920 A | * | 9/2000 | ............ C07C 37/11 |
| JP | 2006089464 A | | 4/2006 | |
| WO | 9962894 | | 12/1999 | |
| WO | 03033566 A1 | | 4/2003 | |
| WO | 2005067904 A1 | | 7/2005 | |
| WO | 2009133278 A1 | | 11/2009 | |
| WO | 2014146750 A1 | | 9/2014 | |

OTHER PUBLICATIONS

Okihama, JP 2000247920 (2000), Machine Translation.*
Kobayashi, JP 3498853 (2004), Machine Translation.*
International Search Report for Corresponding International Application No. PCT/CN2016/076124 dated Jun. 15, 2016, 4 pages.
Hong Duong et al., "Pre-Treatment with the Synthetic Antioxidant T-Butyl Bisphenol Protects Cerebral Tissues from Experimental Ischemia Reperfusion Injury", Journal of Neurochemstry, vol. 130, Dec. 31, 2014, Abstract.
Sasaki et al., "Synthesis of crowded triarylphosphines carrying functional sites" Journal of Organometallic Chemistry, vol. 690, 2005, pp. 2664-2672.
Temin, "Polymers from Bisphenols. Steric Inhibition of Condensation Polymerization", The Journal of Organometallic Chemistry, vol. 26, Jul. 1961, pp. 2518-2521.
Bhowmik et al., "Fully Aromatic Thermotropic Liquid Crystalline Polyesters of Substituted 4,4'-Biphenols. IV. Homopolyesters with Terephthalic Acid and Copolyesters with Terephthalic Acid and 4-Hydroxybenzoic Acid", Journal of Polymer Science: Part A: Polymer Chemistry, vol. 31, Dec. 1993, pp. 2115-2122.
Zhang et al., "Synthesis and characterization of 3, 3', 5, 5'-tetramethyl-4, 4'-di (2-hydroxyethanyoxy)-biphenyl", New Chemical Materials, vol. 39 No. 4. 2011, English Abstract, 4 pages.
Barwell et al., "Substituent Effects in Synthetic Lectins—Exploring the Role of CH-$\pi$ Interactions in Carbohydrate Recognition", The Journal of Organometallic Chemistry, vol. 76, n.d., pp. 6548-6557.
First Office Action and English Translation Thereof for Corresponding CN Application No. 201510016733.9 dated Nov. 30, 2015, 17 pages.
CN Search Report and English Translation Thereof for Corresponding CN Application No. 20150016733.9, 4 pages.
Second Office Action and English Translation Thereof for Corresponding CN Application No. 201510016733.9 dated Jul. 19, 2016, 8 pages.
CN Search Report and English Translation Thereof for Corresponding CN Application No. 20150016733.9, 2 pages.
Australian Office Action for Application No. 2016207118, dated May 4, 2018, 5 pages.
Japanese Office Action and English Translation Thereof for Corresponding JP Application No. 2017-536947 dated Oct. 2, 2018, 12 pages.
Australian Second Office Action for Application No. 2016207118, dated Sep. 7, 2018, 10 pages.
Duong, T.T.H. et al. "Supplementation with a synthetic polyphenol limits oxidative stress and enhances neuronal cell viability in response to hypoxia-re-oxygenation injury", Brain Research, 2008, 1219, 8-18.
Nilsson, A. et al. "Anodic functionalisation in synthesis. Part 1. Methoxylation of methyl-substituted benzene and anisole derivatives, and the synthesis of aromatic aldehydes by anodic oxidation", Journal of Chemical Society Perkin Transactions, 1978, 7, 708-715.
Eichler, B. E. et al. "Three stable 1-silapropadienes", Main Group metal Chemistry, 1999, 22(3), 147-162.
Nilsson et al., "Anodic oxidation of phenolic compounds. Part 5. Anodic methoxylation of phenols. A simple synthesis of quinones, quinone acetals, and 4-methyl-[alpha]-methoxycyclohexa-2, 5-dienones," Journal of the Chemical Society, Perkin Transactions 1, No. 7, Jan. 1, 1978, pp. 696-707.
Miracle et al., "The first stable 1-silaallene," Journal of the American Chemical Society, vol. 115. No. 24, Dec. 1, 1993, pp. 11598-11599.
Extended European Search Report for EP Application No. 16737100.4, dated Mar. 1, 2019, 7 pages.

* cited by examiner ns are considered to play an essential role in ischemic brain injury:

(1) Excitatory Amino Acid Toxicity and Ischemic Brain Damage

BIPHENYL DERIVATIVE AND USES THEREOF

TECHNICAL FIELD

The present invention belongs to the field of pharmaceutical technology and relates to a novel use of a drug, and specifically to a novel use of biphenyl derivatives in the manufacture of a medicament for the treatment and/or prevention of ischemic stroke.

BACKGROUND

In recent years, stroke has become a common disease being serious threat to the health of humans, especially in the elderly over the age of 50, characterized by high incidence, high morbidity, high mortality, high recurrence rate, and multiple complications, i.e. "four-highs and one-multi". In stroke patients, intracerebral arterial stenosis, occlusion or rupture are caused by various predisposing factors, resulting in acute cerebral blood circulation disorders, clinically manifested as a transient or permanent brain dysfunction symptoms and signs.

Statistically, stroke leads to death of 40 million people over the world each year, with an annual incidence of 2 million just in China. Among the 7 million surviving patients, 4.5 million patients lose labor capability to varying degrees as well as self-care capability. The disability rate is as high as 75%. In China, 1.2 million patients die from stroke each year. Those patients who had stroke are prone to have a relapse, and the situation will become worse with each relapse. Therefore, effective means to prevent stroke recurrence are greatly needed.

Ischemic stroke accounts for about 80% of all stroke conditions, which is softening necrosis of local brain tissues due to blood circulation disorders, ischemia, and hypoxia. Its onset is mainly due to atherosclerosis and thrombosis occurring in the arteries that supply blood to the brain, causing stenosis or even occlusion, resulting in focal acute cerebral blood supply insufficiency. Also, foreign objects (solid, liquid, or gas) entering from the blood circulation into the cerebral arteries or the neck arteries that supply to the cerebral blood circulation cause blood flow obstruction or sudden decrease in blood flow volume and consequently brain tissue softening necrosis in the corresponding dominating area.

There are two major causes of ischemic brain injury: (1) due to insufficient productivity after ischemia, ATP-dependent enzyme activity and physiological activities are suppressed, chloride ions, sodium ions and water flow cause cell edema, and synaptic interstitial excitatory amino acids (mainly glutamate) accumulate, resulting in excessive activation of glutamate receptors; with increase in calcium influx mediated by NMDA and other receptors, cell depolarization due to potassium efflux, and opening of voltage-sensitive calcium channels, intracellular calcium overloads and a variety of enzymes including phospholipase and nitric oxide synthase (NOS) are excessively activated, thereby generating a series of active metabolites and free radicals and consequently causing cell damage; (2) ischemic tissues in stroke patients after being treated acquire blood perfusion or spontaneous reperfusion which inevitably lead to cerebral ischemic reperfusion injury, despite of the regaining of nutrients; in other words, although blood supply is restored at a certain time after cerebral ischemia, not only the function thereof fails to recover, but signs of more serious brain dysfunction appear.

Ischemic brain injury involves very complex pathophysiological processes, in which the interactions between the various aspects and various factors have not been fully elucidated. Nevertheless, currently the following mechanisms are considered to play an essential role in ischemic brain injury:

(1) Excitatory Amino Acid Toxicity and Ischemic Brain Damage

A large number of studies have shown that increased excitotoxicity of excitatory amino acid (EAA) during ischemia played an important role in ischemic nerve cell injury. Excitatory amino acids mainly refer to glutamate (Glu) and aspartate (Asp). The postsynaptic neurons overexcited EAA may activate intracellular signal transduction pathways, allowing some receptors to amplify the second messenger effect caused by normal physiological stimuli and triggering the expression of proinflammatory genes after ischemia. Excitatory amino acids such as Glu and Asp play a key role in ischemic nerve cell injury. The longer the ischemic duration, the higher the peak concentration of Glu and Asp in brain interstitial tissues, and the more severe the neuropathological and neurological damages, which is consistent with EAA toxicity being concentration-dependent. The toxic effects of excitatory amino acids on nerve cells are shown in various aspects: excessive EAA activates its receptors, resulting in continuous depolarization of excitatory neurons, which in turn causes intracellular $Ca^{2+}$ overload and consequently lead to cell necrosis; increase in free radical (such as nitric oxide) production is promoted, and cytotoxicity is induced by the free radicals; EAA participates in a variety of metabolic processes in the brain, blocking the tricarboxylic acid cycle and decreasing ATP production, leading to increased cell toxicity by EAA.

(2) Free Radicals and Lipid Peroxidation and Ischemic Brain Damage

Ischemic brain injury is a complex pathophysiological process involving multiple factors. Generally, it is considered to be associated with tissue lipid peroxidation caused by oxygen free radicals and irreversible damage caused by intracellular calcium overload. Its detrimental effects can be summarized as: acting on polyunsaturated fatty acids, and leading to lipid peroxidation; inducing cross-linking of macromolecules such as DNA, RNA, polysaccharides, and amino acids, with the original activity or function of the cross-linked macromolecules being lost or attenuated; promoting the polymerization and degradation of polysaccharide molecules; free radicals widely attacking unsaturated fatty acid-rich nerve membranes and blood vessels, inducing a lipid peroxidation waterfall effect, resulting in protein denaturation, breaking of polynucleotide strands, and base remodification, causing damage to cell structure integrity, and seriously affecting membrane permeability, ion transportation, and membrane barrier function, thereby leading to cell death. Free radicals also evoke an increase in EAA release, leading to reperfusion injury after cerebral ischemia.

(3) $Ca^{2+}$ Overload and Cerebral Ischemic Brain Injury $Ca^{2+}$ overload in ischemic brain injury is a result of the combined effects of various factors, and is a common pathway for the action of various factors in the process of cerebral ischemic injury. The impact of $Ca^{2+}$ in ischemic brain injury mainly includes:

a) Mitochondrial Dysfunction: When the Intracellular and Extracellular Calcium balance is disrupted, extracellular $Ca^{2+}$ flows into cells and mainly accumulate in mitochondria, and $Ca^{2+}$ may inhibit ATP synthesis, impeding energy generation. $Ca^{2+}$ activates phospholipases on mitochondria, causing mitochondrial membrane damage. In addition to ATP synthesis, mitochondria play an important role in cellular redox reactions and maintenance of osmotic pressure, pH value, and cytoplasmic signals, and mitochondria is the important target of cell damage.

b) Enzyme activation: $Ca^{2+}$ activates $Ca^{2+}$-dependent phospholipases (mainly phospholipase C and phospholipase A2) and promote membrane phospholipid degradation; the free fatty acids, prostaglandins, leukotrienes, lysophospholipids and the like that are produced in the process of membrane phospholipid degradation are toxic to cells; $Ca^{2+}$ also activates calcium-dependent proteases and converts the intracellular non-toxic xanthine dehydrogenase into xanthine oxidase, with large amounts of oxygen free radicals generated; $Ca^{2+}$ may activate NOS.

It has been demonstrated in experiments that the above pathophysiological changes could somehow be intervened by drugs. Compared to patients with drug withdrawal, those with long-term use of reliable drugs for prevention and treatment of ischemic stroke have their recurrence rate reduced by 80% or more and mortality reduced by 90% or more. Among patients who have taken medication for a long time over three years, 80% or more is not at risk of recurrence, and very few shows slight recurrence. This has provided a theoretical foundation for medicinally combating ischemic brain injury. Currently, commonly used drugs against cerebrovascular diseases mainly include the following categories:

NMDA receptor antagonists: antagonizing NMDA receptors, thereby inhibiting calcium influx mediated by them; a representative drug is MK801;

Calcium ion antagonists: preventing intracellular calcium overload, preventing vasospasm, and increasing blood flow; a representative drug is nimodipine;

Anti-free radicals drugs: scavenging free radicals, inhibiting lipid peroxidation, thereby inhibiting oxidative damage to brain cells, vascular endothelial cells and nerve cells; a representative drug is edaravone.

However, the specific mechanism of ischemic stroke has not been clarified and is considered to be a very complex pathophysiological process with interaction of many factors; whereas, the above drugs act by simple mechanisms, with uncertain clinical therapeutic effects or serious side effects, so that their application in the treatment of ischemic stroke is limited.

In recent years, many domestic and foreign studies have found that the anesthetic propofol may have a very positive impact on ischemic stroke. In animal and in vitro experiments, and even in some clinical studies, propofol has been proven to have significant protective and therapeutic effects on neurological impairment. It has been demonstrated in the experiments that propofol could not only block the sodium ion flow or reduce Glu release activated by potassium ions by activating the GABA receptor, but also block the inhibition of Glu transportation by glial cells after oxidative treatment, both eventually reducing extracellular Glu concentration, delaying or preventing excitatory neuron death; propofol could inhibit extracellular calcium influx through voltage-dependent calcium channels, which could increase the current inactivation rate of L-type voltage-dependent calcium channels to a certain extent, thereby reducing calcium influx; propofol could bind to GABAa receptor-specific sites, not only to increase the frequency of the opening of chloride channel by GABA, but also to enhance the binding of GABA binding sites with low affinity to GABA by positive allosteric regulation; propofol can inhibit the production of inflammatory cytokines such as TNF, IL-1 and IL-6 in the blood of patients with sepsis and had a strong inhibitory effect even at lower concentrations; propofol could inhibit the expression of the pro-apoptotic gene caspase-3 mRNA and enhance the expression of the anti-apoptotic gene Bcl-2 mRNA in brain tissues; propofol could competitively bind to membrane phospholipids, and form a stable phenoxy moiety with peroxide, which in fact forms free radicals of low activities in place of the free radicals of high activities, thereby reducing the lipid peroxidation cascade induced by the latter. The above results suggest that the mechanism by which propofol fight ischemic stroke may include anti-free radical effect, inhibition of lipid peroxidation, inhibition of intracellular calcium overload, and inhibition of cellular apoptosis. However, the clinical use of propofol in the treatment of ischemic stroke is restricted due to the general anesthetic effect thereof.

SUMMARY OF THE INVENTION

It is an object of the present invention to provide a biphenyl derivative or a pharmaceutically acceptable salt or solvate thereof having therapeutic effect on ischemic stroke.

In order to achieve the above object, the present invention provides a biphenyl derivative represented by the formula (I) or a pharmaceutically acceptable salt or solvate thereof

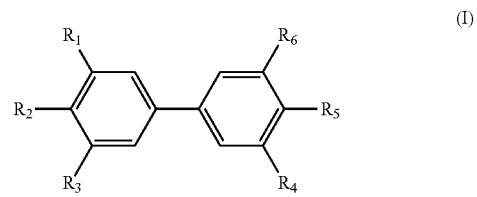

wherein $R_1$, $R_3$, $R_4$, and $R_6$ in the biphenyl derivative are each independently an alkyl group having 1 to 8 carbon atoms, preferably each independently an alkyl group having 2 to 6 carbon atoms;

$R_2$ may be selected from optionally substituted hydroxyl, optionally substituted carboxyl, optionally substituted acyl or ester group, and halogen;

$R_5$ may be selected from optionally substituted hydroxyl, optionally substituted carboxyl, optionally substituted acyl or ester group, and halogen;

with the proviso that when $R_2$ and $R_5$ are both hydroxyl, $R_1$, $R_3$, $R_4$, and $R_6$ are not simultaneously isopropyl.

Preferably, $R_1$, $R_3$, $R_4$, and $R_6$ in the biphenyl derivative are each independently an alkyl having 1 to 8 carbon atoms, preferably each independently an alkyl having 2 to 6 carbon atoms;

$R_2$ is selected from optionally substituted hydroxyl, optionally substituted carboxyl, optionally substituted acyl or ester group, and halogen;

$R_5$ is selected from optionally substituted carboxyl, optionally substituted acyl or ester group, alkoxy, and halogen.

The optionally substituted hydroxyl group according to the present invention refers to —OH, or a group in which the hydrogen in —OH is substituted.

The optionally substituted carboxyl group according to the present invention refers to —COOH, or a group in which the hydrogen in —COOH is substituted.

The optionally substituted acyl and ester group according to the present invention refer to groups in which hydrogen in —C(=O)H, —OC(=O)H is substituted.

It is further preferred that $R_1$, $R_3$, $R_4$, and $R_6$ in the biphenyl derivative are each independently n-propyl, isopropyl, n-butyl, isobutyl, or sec-butyl;

$R_2$ may be selected from optionally substituted hydroxyl, optionally substituted carboxyl, optionally substituted acyl or ester group, and halogen;

$R_5$ may be selected from optionally substituted carboxyl, optionally substituted acyl or ester group, and halogen.

It is further preferred that $R_1$, $R_3$, $R_4$, and $R_6$ in the biphenyl derivative are each independently n-propyl or isopropyl;

$R_2$ may be selected from optionally substituted hydroxyl, optionally substituted carboxyl, optionally substituted acyl or ester group, and halogen;

$R_5$ may be selected from optionally substituted carboxyl, optionally substituted acyl or ester group, and halogen.

It is further preferred that $R_1$, $R_3$, $R_4$, and $R_6$ in the biphenyl derivative are each independently isopropyl;

$R_2$ may be selected from optionally substituted hydroxyl, optionally substituted carboxyl, optionally substituted acyl or ester group, and halogen;

$R_5$ may be selected from optionally substituted carboxyl, optionally substituted acyl or ester group, and halogen.

It is further preferred that $R_1$, $R_3$, $R_4$, and $R_6$ in the biphenyl derivative are each independently n-butyl, isobutyl, or sec-butyl;

$R_2$ may be selected from optionally substituted hydroxyl, optionally substituted carboxyl, optionally substituted acyl or ester group, and halogen;

$R_5$ may be selected from optionally substituted carboxyl, optionally substituted acyl or ester group, and halogen.

It is further preferred that $R_1$, $R_3$, $R_4$, and $R_6$ in the biphenyl derivative are each independently a C5 alkyl or C6 alkyl;

$R_2$ may be selected from optionally substituted hydroxyl, optionally substituted carboxyl, optionally substituted acyl or ester group, and halogen;

$R_5$ may be selected from optionally substituted carboxyl, optionally substituted acyl or ester group, and halogen.

It is further preferred that $R_1$, $R_3$, $R_4$, and $R_6$ in the biphenyl derivatives of the present invention are each independently selected from $C_{1-8}$ alkyl, preferably $C_{2-6}$ alkyl;

$R_2$ is selected from hydroxyl, carboxyl, halogen, $R_7O$—, or $R_8C(O)O$—;

$R_5$ is selected from carboxyl, halogen, $R_7O$— or $R_8C(O)O$—;

$R_7$ is $C_{1-3}$ alkyl, and the $C_{1-3}$ alkyl is unsubstituted or substituted with one or more $R_9C(=O)O$— and $(NaO)_2P(=O)O$—, wherein $R_9$ is methyl, ethyl, or n-propyl;

$R_8$ is selected from hydrogen, $R_{10}R_{11}N$—, or $C_{1-4}$ alkyl; the $C_{1-4}$ alkyl is unsubstituted or substituted with one or more amino or carboxyl; $R_{10}$ and $R_{11}$ are each independently selected from hydrogen, methyl, ethyl, or n-propyl. Preferably, $R_1$, $R_3$, $R_4$, and $R_6$ are each independently selected from n-propyl, isopropyl, n-butyl, isobutyl, or sec-butyl; more preferably, $R_1$, $R_3$, $R_4$, and $R_6$ are each independently selected from n-propyl or isopropyl; further preferably, $R_1$, $R_3$, $R_4$, and $R_6$ are all isopropyl; $R_9$ is methyl; $R_{10}$ and $R_{11}$ are each independently methyl; and the $C_{1-4}$ alkyl is methyl, ethyl, n-propyl, isopropyl, or isobutyl.

According to a specific embodiment of the present invention, the biphenyl derivative of the present invention has a structure represented by the formula (I-1):

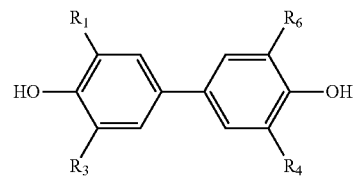

wherein $R_1$, $R_3$, $R_4$, and $R_6$ are alkyls having 2 to 6 carbon atoms, wherein at least one is not isopropyl.

Preferably, $R_1$, $R_3$, $R_4$, and $R_6$ in formula (1) are n-propyl or isopropyl.

Preferably, $R_1$, $R_3$, $R_4$, and $R_6$ in formula (1) are C5 alkyl or C6 alkyl.

According to a specific embodiment of the present invention, the biphenyl derivative has the following structure:

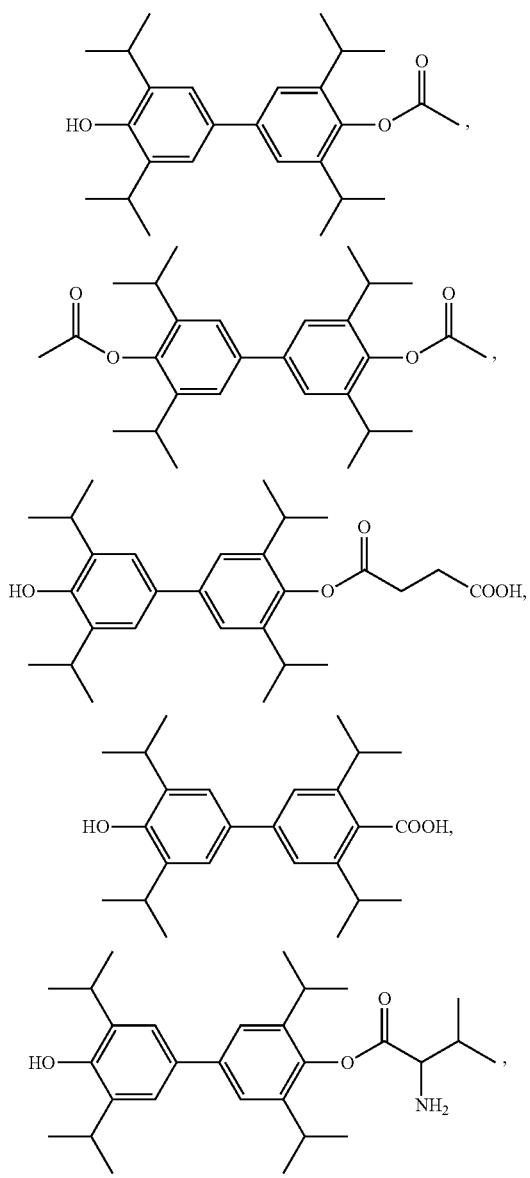

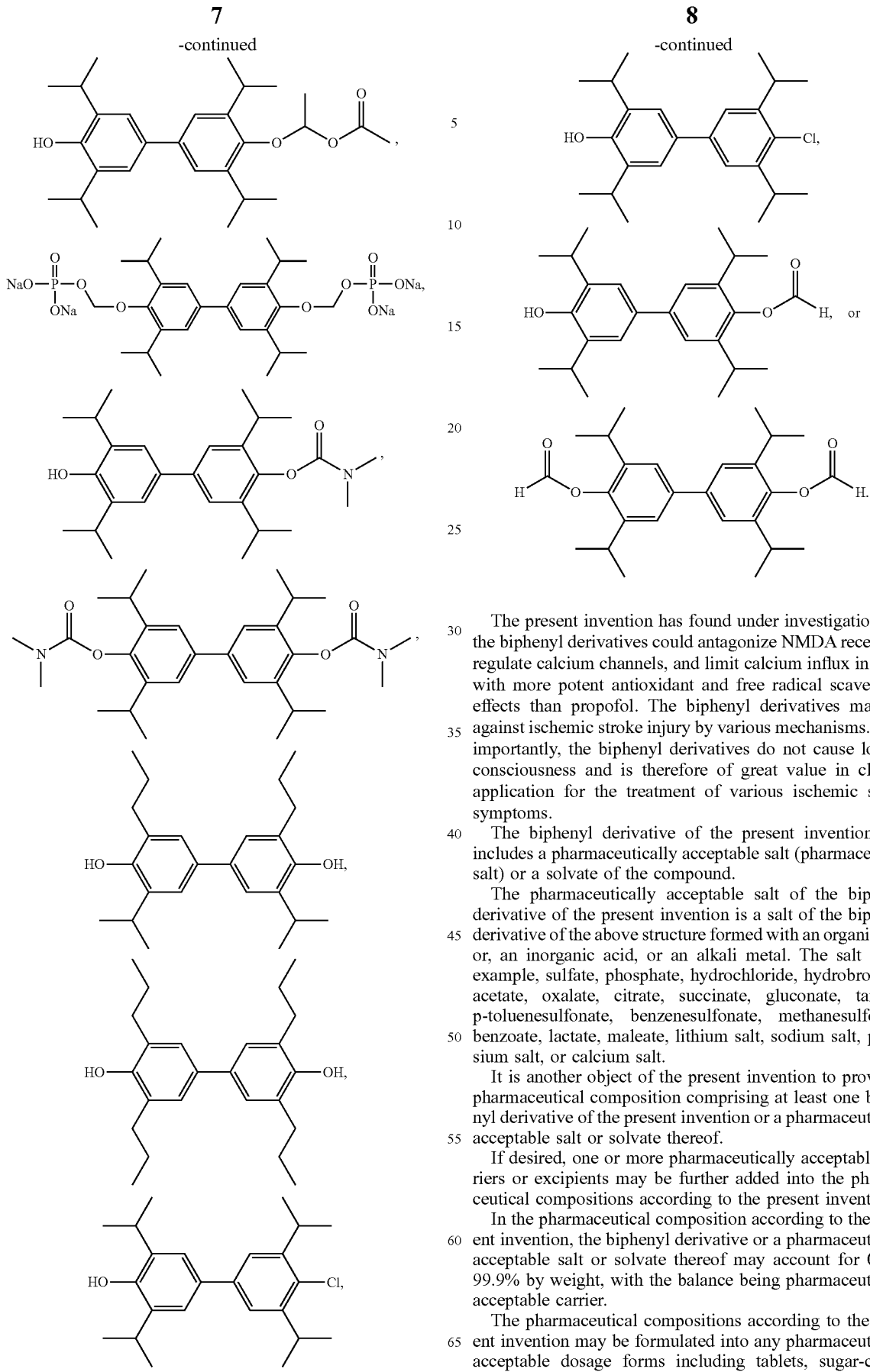

The present invention has found under investigation that the biphenyl derivatives could antagonize NMDA receptors, regulate calcium channels, and limit calcium influx in cells, with more potent antioxidant and free radical scavenging effects than propofol. The biphenyl derivatives may act against ischemic stroke injury by various mechanisms. Most importantly, the biphenyl derivatives do not cause loss of consciousness and is therefore of great value in clinical application for the treatment of various ischemic stroke symptoms.

The biphenyl derivative of the present invention also includes a pharmaceutically acceptable salt (pharmaceutical salt) or a solvate of the compound.

The pharmaceutically acceptable salt of the biphenyl derivative of the present invention is a salt of the biphenyl derivative of the above structure formed with an organic acid or, an inorganic acid, or an alkali metal. The salt is for example, sulfate, phosphate, hydrochloride, hydrobromide, acetate, oxalate, citrate, succinate, gluconate, tartrate, p-toluenesulfonate, benzenesulfonate, methanesulfonate, benzoate, lactate, maleate, lithium salt, sodium salt, potassium salt, or calcium salt.

It is another object of the present invention to provide a pharmaceutical composition comprising at least one biphenyl derivative of the present invention or a pharmaceutically acceptable salt or solvate thereof.

If desired, one or more pharmaceutically acceptable carriers or excipients may be further added into the pharmaceutical compositions according to the present invention.

In the pharmaceutical composition according to the present invention, the biphenyl derivative or a pharmaceutically acceptable salt or solvate thereof may account for 0.1 to 99.9% by weight, with the balance being pharmaceutically acceptable carrier.

The pharmaceutical compositions according to the present invention may be formulated into any pharmaceutically acceptable dosage forms including tablets, sugar-coated tablets, film-coated tablets, enteric-coated tablets, capsules, hard capsules, soft capsules, oral liquid, oral agents, granules, electuary, pills, powders, paste, pellets, suspensions, powders, solution, injection, suppositories, ointment, plaster, cream, spray, drops, and patches. The formulations according the present invention are preferably tablets, capsules, injection, emulsion, liposomes, lyophilized powders or microsphere formulations. The capsules are, for example, soft capsules. The microsphere preparation is a new drug dosage form which is a solid skeleton of a micro-spherical entity formed by coating and solidifying a solid or liquid drug with a polymer material such as starch, chitosan, polylactic acid, or gelatin as a carrier, having varying diameters generally in the range of 1 to 300 μm or even larger, which belongs to a matrix-type skeleton particle.

An orally administered formulation of the pharmaceutical composition according to the present invention may contain conventional excipients such as binders, fillers, diluents, tablets, lubricants, disintegrants, colorants, flavoring agents, and/or wetting agents. If necessary, tablets may be coated.

Suitable fillers include cellulose, mannitol, lactose and the like. Suitable disintegrants include starch, polyvinylpyrrolidone, and starch derivatives such as sodium starch glycolate. Suitable lubricants include magnesium stearate. Suitable pharmaceutically acceptable wetting agents include sodium dodecyl sulfate.

Solid oral compositions can be prepared by conventional methods such as mixing, filling, tabletting and the like. Repeated mixing allows the active agents to be distributed throughout the composition with a large amount of filler.

The form of the oral liquid formulation may be, for example, an aqueous or oily suspension, solution, emulsion, syrup, or elixir, or may be a dry product that can be reconstituted with water or other suitable carriers prior to use. Such liquid formulations may contain conventional additives such as suspending agents, emulsifying agents, non-aqueous carriers, preservatives and the like, and may contain conventional flavoring or coloring agents, if desired. The suspending agent is, for example, sorbitol, syrup, methylcellulose, gelatin, hydroxyethylcellulose, carboxymethylcellulose, aluminum stearate gel, and/or hydrogenated edible fats. The emulsifier is, for example, lecithin, sorbitan monooleate and/or arabic gum. The non-aqueous carriers (which may include edible oils) are, for example, almond oil, fractionated coconut oil, oily esters such as glycerol esters, propylene glycol and/or ethanol. The preservatives are, for example, parabens or propylparaben and/or sorbic acid.

As for injection, a liquid unit dosage form as prepared contains the active agent of the present invention (i.e., the biphenyl derivatives according to the present invention and a pharmaceutically acceptable salt or solvate thereof) and a sterile carrier. Depending on the carrier and concentration, the compound may be suspended or dissolved therein. The solution is usually prepared by dissolving the active agent in a carrier, which is filtered and sterilized before being loaded into a suitable vial or ampoule and then sealed. An adjuvant such as a local anesthetic, a preservative, and a buffer may also be dissolved in such a carrier. In order to improve its stability, the composition may be frozen after being loaded in a vial and water is removed under vacuum.

A suitable pharmaceutically acceptable carrier may be optionally added to the pharmaceutical composition according to the present invention when prepared as a medicament. The pharmaceutically acceptable carrier is selected from mannitol, sorbitol, sodium metabisulfite, sodium bisulfite, sodium thiosulfate, cysteine hydrochloride, mercaptoacetic acid, methionine, vitamin C, EDTA disodium, EDTA calcium sodium, monovalent alkali metal carbonate, acetate, phosphate or aqueous solution thereof, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivatives, cellulose and its derivatives, alginate, gelatin, polyvinylpyrrolidone, glycerol, Tween 80, agar, calcium carbonate, calcium bicarbonate, surfactant, polyethylene glycol, cyclodextrin, β-cyclodextrin, phospholipid materials, kaolin, talc, calcium stearate and/or magnesium stearate.

Preferably, the pharmaceutical excipients according to the present invention may include polyethylene glycol, phospholipids, vegetable oils, vitamin E and/or glycerol;

The phospholipid may be selected from one or more of soybean phospholipids, egg yolk lecithin and hydrogenated phospholipids;

The vegetable oil may be selected from one or more of soybean oil, olive oil and safflower oil.

Another object of the present invention is to provide use of the biphenyl derivative or a pharmaceutically acceptable salt or solvate thereof or the pharmaceutical composition according to the present invention in the manufacture of medicaments for the treatment and/or prevention of ischemic stroke.

The ischemic stroke described in the present invention include injury caused by the following conditions: cerebral thrombosis, transient ischemic attack, basal ganglia infarction, atherosclerotic thrombotic cerebral infarction, lacunar infarction, cerebral embolism, and brain vascular dementia. The above conditions usually cause headache, dizziness, tinnitus, hemiplegia, swallowing difficulty, babbling, nausea, vomiting, coma and the like.

The "treatment and/or prevention of ischemic stroke" according to the present invention generally refers to the treatment and/or prevention of the injury caused by ischemic stroke.

The use of the present invention is realized by improving the neurological impairment upon ischemic reperfusion.

The use of the present invention is realized by reducing the volume of ischemic reperfusion cerebral infarction.

The use of the present invention is realized by reducing the consumption of endogenous oxygen free radical scavenger SOD, reducing lipid peroxidation damage, and at the same time lowering the serum MDA content.

The use of the present invention is realized by effectively down-regulating the cellular expression of Fas in brain tissues.

The use of the present invention is realized by effectively inhibiting brain cell apoptosis.

The use of the present invention is realized by effectively down-regulating the cellular expression of IL-1β and TNF-α in brain tissues.

The treatment and/or prevention of ischemic stroke according to the present invention is achieved by: improving cerebral ischemia and/or reperfusion neurological impairment; reducing cerebral ischemia and/or reperfusion cerebral infarction volume; reducing the endogenous oxygen free radical scavenger SOD consumption in brain tissues, reducing lipid peroxidation damage, while reducing serum MDA content; down-regulating cellular Fas expression in brain tissues; inhibiting brain cell apoptosis; and/or down-regulating cellular IL-1β and TNF-α expression in brain tissues.

In the Embodiments of the present invention, a middle cerebral artery occlusion animal model (MCAO) established by the inventor using the suture method has the advantages of no craniotomy, less trauma, accurate control of the ischemia and reperfusion time, and is currently the most classic model of focal cerebral ischemic reperfusion. This model has been widely used domestically and abroad in cerebral ischemia experiments and evaluation of medicaments for treating cerebral ischemic reperfusion injury.

Upon cerebral ischemic reperfusion, intracellular oxygen free radicals increase significantly and are particularly prone to attack biomembrane structures comprising unsaturated double bonds, so as to induce lipid peroxidation which disrupt the membrane structures, affect membrane permeability, and lead to a series of pathophysiological changes to ion transportation, bioenergy generation and organelle functions, resulting in damages to nerve cells, glial cells, and vascular endothelial cells. SOD is the primary enzymatic defense mechanism against intracellular oxygen free radicals, which scavenges the superoxide anion radicals by disproportionation. Change in the content of MDA, a metabolite of the lipid peroxidation reaction of oxygen free radicals with biomembrane unsaturated fatty acids, indirectly reflects the content of oxygen free radicals and the degree of cell damage in tissues. Therefore, determination of the SOD activity and the MDA content in ischemic reperfusion can reflect the extent of the lipid peroxidation reaction induced by free radicals in vivo.

Cerebral ischemic reperfusion injury is primarily related to response to oxidative stress, inflammatory response, calcium overload, cerebral edema, and apoptosis. Upon cerebral ischemic reperfusion, due to energy metabolism and the action of various endogenous active substances, $Ca^{2+}$ release from the reservoir is stimulated and intracellular $Ca^{2+}$ concentration increase. Also, cerebral ischemia can cause EAA to be excessively released from neuronal or glial cell transmitter pool or metabolic pool. EAA can induce intracellular $Ca^{2+}$ overload, resulting in increased free radical generation. The increase of free radicals and EAA may both induce the expression of apoptotic factors such as Fas after cerebral ischemic reperfusion, thereby promoting cell apoptosis. As such, cell apoptosis status can also reflect the degree of damage to brain cells. IL-1β and TNF-α are the major proinflammatory factors after brain injury and participate in the inflammatory response in ischemic and reperfusion regions. After cerebral ischemic reperfusion, the inflammatory cells in the vicinity of the endothelial cells, neurons, astrocytes, and blood vessels in the injured area are activated, triggering an inflammatory response by releasing IL-1β and TNF-α and therefore resulting in neuronal damage. Measurement of the contents of IL-1β and TNF-α as the starting factors in inflammatory response is of great significance for the evaluation of brain injury after ischemic reperfusion.

Meanwhile, because the occurrence of reperfusion in stroke patients is often delayed, the brain tissue ischemic "hunger" injury cannot be ignored either. Thus, the present invention also evaluate the protective effect of the biphenyl derivative according to the present invention in permanent ischemic injury by using the middle cerebral artery occlusion animal model (MCAO) established by the suture method.

It is demonstrated with experiments in the present invention: the biphenyl derivative according to the present invention can effectively reduce the consumption of the endogenous oxygen free radical scavenger SOD activity due to cerebral ischemic reperfusion injury, reduce lipid peroxidation damage, reduce serum MDA content, effectively down-regulate Fas expression, reduce apoptotic cells, and reduce the expression of the proinflammatory cytokines IL-1β and TNF-α, so as to achieve protection of the rat neurons against cerebral ischemic reperfusion, and also have a protective effect on permanent cerebral ischemic injury, showing a prominent therapeutic effect.

In another aspect, the present invention provides a method for treating and/or preventing ischemic stroke in animal or human comprising administering to an animal or human subject an effective amount of the biphenyl derivative and a pharmaceutically acceptable salt or solvate thereof according to the present invention or the pharmaceutical composition according to the present invention.

In the method according to the present invention, preferably, the treatment and/or prevention of ischemic stroke is achieved by: improving cerebral ischemia and/or reperfusion neurological impairment; reducing cerebral ischemia and/or reperfusion cerebral infarction volume; reducing the endogenous oxygen free radical scavenger SOD consumption in brain tissues, reducing lipid peroxidation damage, while reducing serum MDA content; down-regulating cellular Fas expression in brain tissues; inhibiting brain cell apoptosis; and/or down-regulating cellular IL-1β and TNF-α expression in brain tissues.

Preferably, in the method according to the present invention, the ischemic stroke includes damage caused by one or more of the following conditions: cerebral thrombosis, transient ischemic attack, basal ganglia infarction, atherosclerotic thrombotic cerebral infarction, lacunar cerebral infarction, cerebral embolism, and cerebrovascular dementia.

DETAILED DESCRIPTION OF THE INVENTION

The present invention will be further described with reference to the following examples. It is to be understood that these examples are merely illustrative of the invention and are not intended to limit the scope of the invention.

EXAMPLE 1

Compound 1: 4'-hydroxy-3,3',5,5'-tetraisopropylbiphenyl-4-acetate

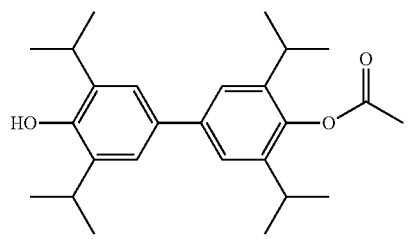 [SMILES: CC(=O)Oc1c(C(C)C)cc(-c2cc(C(C)C)c(O)c(C(C)C)c2)cc1C(C)C]

Preparation procedure: 4'-Benzyloxy-3,3',5,5'-tetraisopropylbiphenyl-4-acetate (5 g, 10.27 mmol) was dissolved in 200 mL methanol at room temperature, 10% palladium carbon (570 mg) was then added thereto, evacuated to vacuum and charged with hydrogen, which was repeated three times, and then sealed and reacted at room temperature for 10 h. The palladium-carbon in the reaction solution was filtered, and the filtrate was evaporated under reduced pressure to give 4'-hydroxy-3,3',5,5'-tetraisopropylbiphenyl-4-acetate (3.9 g, 95.73%) as white solid. $^1$H NMR (300 MHz, $CDCl_3$) δ 7.19 (s, 4H), 4.86 (s, 1H), 3.37-3.32 (m, 4H), 3.16 (s, 3H), 1.20 (d, 24H).

EXAMPLE 2

Compound 2: 3,3',5,5'-tetraisopropylbiphenyl-4'-diacetate

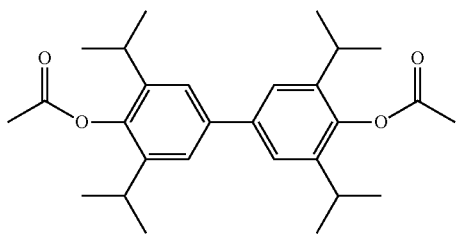 [SMILES: CC(=O)Oc1c(C(C)C)cc(-c2cc(C(C)C)c(OC(C)=O)c(C(C)C)c2)cc1C(C)C]

Preparation procedure: 4,4'-dihydroxy-3,3',5,5'-tetraisopropylbiphenyl (5 g, 14.10 mmol) was added to 30 mL acetic anhydride and allowed to reflux for 3 h under nitrogen. The reaction solution was cooled to room temperature and the acetic anhydride was removed under reduced pressure. Water (200 mL) was added to the residue to give a white solid which was washed with 10% cold ethanol (100 mL) and water (200 mL) and dried to obtain 3,3',5,5'-tetraisopropylbiphenyl-4'-diacetate (6 g, 95.06%), as white solid. $^1$H NMR (300 MHz, CDCl$_3$) δ 7.19 (s, 4H), 2.91-2.89 (m, 4H), 2.32 (s, 6H), 1.19 (d, 24H).

EXAMPLE 3

Compound 3: 3,3',5,5'-tetraisopropylbiphenyl-4,4'-bis(oxymethylene phosphate)

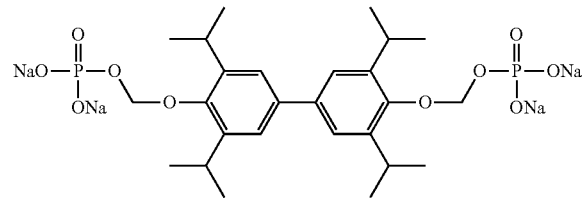

(1) 4,4'-dihydroxy-3,3',5,5'-tetraisopropylbiphenyl (0.5 g, 1.4 mmol) was dissolved in dry THF (10 mL), solid NaOH (0.224 g, 5.6 mmol) and bromochloromethane (8.185 g, 84 mmol) was added thereto, and then refluxed under N$_2$ for 2 h. The reaction solution was cooled to room temperature, filtered, and concentrated to give a yellow oil as intermediate.

(2) Triethylamine (1.4 mL, 11.03 mmol) and 85% phosphoric acid (0.5 mL, 8.9 mmol) was added sequentially to 10 mL of anhydrous acetonitrile. The intermediate obtained in (1) was added to the acetonitrile solution under stirring, and then reacted at 65° C. for 2 h. The reaction solution was cooled to room temperature, the solvent was evaporated, and the residue was dissolved in 15 mL of water, adjusted to pH=1.5 with 8 M HCl, and extracted with anhydrous ether. The organic phase was combined, washed with saturated sodium chloride, dried over anhydrous sodium sulfate, and concentrated to give a yellow oil.

(3) 5 mL of water was added to the above oil, adjusted to pH 9 with 20% sodium hydroxide solution, and extracted twice with toluene. The aqueous phase was concentrated to ½ volume, and 9 mL of isopropanol was added. The mixture was heated at 70° C. until the solution became transparent, and then cooled to 0° C. White solid was precipitated, filtered, and dried under vacuum at 45° C. to give 3,3',5,5'-tetraisopropylbiphenyl-4,4'-bis(oxymethylenephosphate) (50 mg, 5%). $^1$H NMR (300 MHz, D$_2$O) δ 7.29 (s, 4H), 5.20 (s, 4H), 3.36-3.12 (m, 4H), 1.12 (d, 24H).

EXAMPLE 4

Compound 4: 4'-hydroxy-3,3',5,5'-tetraisopropylbiphenyl-4-dimethyl carbamate, and compound 5: 3,3',5,5'-tetraisopropylbiphenyl-4,4'-bis(dimethylcarbamate)

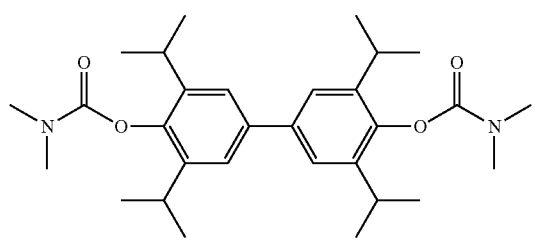

3,3',5,5'-tetraisopropylbiphenyl-4,4'-bis(dimethylcarbamate)

4,4'-dihydroxy-3,3',5,5'-tetraisopropylbiphenyl (1.0 g, 2.8 mmol) was dissolved in methylene chloride, solid sodium hydroxide (0.112 g, 2.8 mmol) was added thereto under stirring, and then N,N-dimethylformyl chloride (0.3 mL, 2.8 mmol) was added slowly and refluxed for 3 h. The solvent was evaporated to dryness, water was added, and the mixture was extracted with ethyl acetate, washed with saturated sodium chloride, dried over anhydrous sodium sulfate, and concentrated to give a yellow oil which was then purified with petroleum ether-ethyl acetate eluent and recrystallized from petroleum ether-ethyl acetate to give 4'-hydroxy-3,3',5,5'-tetraisopropylbiphenyl-4-dimethyl carbamate (0.36 g, 30.2%) as a white solid and 3,3',5,5'-tetraisopropylbiphenyl-4,4'-bis(dimethylcarbamate) (0.31 g, 22.3%) as a white solid.

4'-hydroxy-3,3',5,5'-tetraisopropylbiphenyl-4-dimethylcarbamate: white solid. $^1$H NMR (300 MHz, CDCl$_3$) δ 7.16 (s, 2H), 7.12 (s, 2H), 4.82 (s,1H), 3.11 (s,6H), 2.98-2.93 (m, 4H), 1.20 (d, 24H).

3,3',5,5'-tetraisopropylbiphenyl-4,4'-bis(dimethylcarbamate): white solid. $^1$H NMR (300 MHz, CDCl$_3$) δ 7.18 (s, 4H), 3.12 (s, 12H), 2.98-2.94 (m, 4H), 1.22 (d, 24H).

EXAMPLE 5

Compound 6: [4-(4'-hydroxy-3,3',5,5'-tetraisopropylbiphenyl)oxy]-4-carbonyl butyric acid

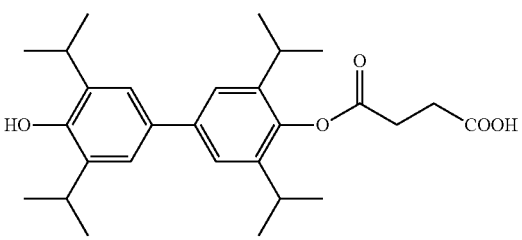 [SMILES: CC(C)c1cc(-c2cc(C(C)C)c(OC(=O)CCC(=O)O)c(C(C)C)c2)cc(C(C)C)c1O]

4,4'-dihydroxy-3,3',5,5'-tetraisopropylbiphenyl (5.00 g, 14.10 mmol) was dissolved in DMSO (20 mL), and succinic anhydride (1.41 g, 14.09 mmol) was then added thereto and heated at 90° C. for a reaction for 5 h. The reaction solution was cooled to room temperature, into which water was added, extracted with ethyl acetate, dried over anhydrous sodium sulfate, and filtered to remove sodium sulfate. The filtrate was purified with petroleum ether-ethyl acetate eluent to give [4-(4'-hydroxy-3,3',5,5'-tetraisopropylbiphenyl) oxy]-4-carbonylbutyric acid (3.50 g, 54.59%) as a white solid. $^1$H NMR (300 MHz, CDCl$_3$) δ 11.10 (s, 1H), 7.65 (s, 2H), 7.51 (s, 2H), 5.35 (s, 1H), 3.07-3.04 (m, 4H), 2.71 (s, 4H), 1.20-1.18 (d, 24H).

EXAMPLE 6

Compound 7: 4,4'-dihydroxy-3,3'-diisopropyl-5,5'-dipropylbiphenyl

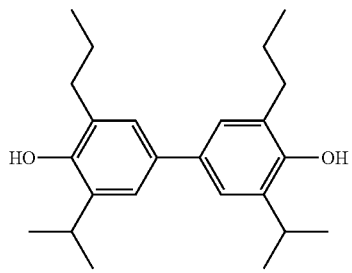 [SMILES: CCCc1cc(-c2cc(CCC)c(O)c(C(C)C)c2)cc(C(C)C)c1O]

(1) O-isopropylphenol (1.0 g, 7.3 mmol) and allyl bromide (14.6 mmol) were successively added to a 25 mL round bottom flask and dissolved in dichloromethane.

(2) Benzyl tributyl ammonium bromide (0.26 g, 0.73 mmol) was added to another 50 mL flask and dissolved in a 1 M NaOH solution.

(3) The solution obtained in (1) was added slowly to the solution obtained in (2) at room temperature and stirred at room temperature for 2 h. The organic phase was separated, and the aqueous phase was extracted with dichloromethane. The organic phases were combined, washed with water and saturated sodium chloride, dried over anhydrous sodium sulfate, and concentrated to give a colorless liquid. The liquid was heated under nitrogen at 250° C. for 2 h, cooled and purified with column chromatography to give a colorless liquid. The colorless liquid was dissolved in absolute ethanol and reduced by addition of Pd/C to give 2-isopropyl-6-propylphenol: $^1$H NMR (400 MHz, CDCl$_3$) δ 7.06 (dd, J=7.6, 1.6 Hz, 1H), 6.97 (dd, J=7.5, 1.6 Hz, 1H), 6.85 (t, J=7.6 Hz, 1H), 4.75 (s, 1H), 3.22-3.13 (m, 1H), 2.59-2.54 (m, 2H), 1.72-1.59 (m, 2H), 1.26 (d, J=6.9 Hz, 6H), 0.99 (t, J=7.3 Hz, 3H).

(4) The obtained liquid (1.0 g, 5.6 mmol) was dissolved in 20 mL of dichloromethane, into which the catalyst Cu(OH)Cl.TMEDA (50 mg, 0.1 mmol) was added, and stirred at room temperature to give a red solid quinone which was then reduced with sodium hydrosulfite to give 4,4'-dihydroxy-3,3'-diisopropyl-5,5'-dipropylbiphenyl (1.1 g, 55.5%).

4,4'-dihydroxy-3,3'-diisopropyl-5,5'-dipropylbiphenyl: $^1$H NMR (300 MHz, CDCl$_3$) δ 7.29 (s, 4H), 6.52 (s, 2H), 3.13-3.08 (m, 2H), 2.43-2.40 (m, 4H), 1.51-1.43 (m, 4H), 1.03 (d, 12H), 0.84-0.81 (m, 6H).

EXAMPLE 7

Compound 8: 4,4'-dihydroxy-3,3',5,5'-tetrapropylbiphenyl

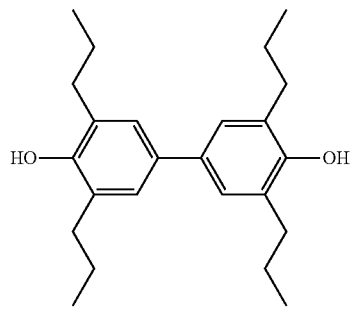 [SMILES: CCCc1cc(-c2cc(CCC)c(O)c(CCC)c2)cc(CCC)c1O]

(1) O-isopropylphenol (1.0 g, 7.3 mmol) and allyl bromide (14.6 mmol) were successively added to a 25 mL round bottom flask and dissolved in dichloromethane.

(2) Benzyl tributyl ammonium bromide (0.26 g, 0.73 mmol) was added to another 50 mL flask and dissolved in a 1 M NaOH solution.

(3) The solution obtained in (1) was added slowly to the solution obtained in (2) at room temperature and stirred at room temperature for 2 h. The organic phase was separated, and the aqueous phase was extracted with dichloromethane. The organic phases were combined, washed with water and saturated sodium chloride, dried over anhydrous sodium sulfate, and concentrated to give a colorless liquid. The liquid was heated under nitrogen at 250° C. for 2 h, cooled and purified with column chromatography to give a colorless liquid. The colorless liquid was dissolved in absolute ethanol and reduced by addition of Pd/C to give 2,6-dipropylphenol: $^1$H NMR (400 MHz, CDCl$_3$) δ 7.06 (t, J=7.6, Hz, 1H), 6.94 (dd, J=7.6, 1.6 Hz, 2H), 5.35 (s, 1H), 2.62 (t, 4H), 1.68-1.59 (m, 4H), 0.90 (t, J=7.3 Hz, 6H).

(4) The obtained liquid (1.0 g, 5.6 mmol) was dissolved in 20 mL of dichloromethane, into which the catalyst Cu(OH)Cl.TMEDA (50 mg, 0.1 mmol) was added, and stirred at room temperature to give a red solid quinone which was then reduced with sodium hydrosulfite to give 4,4'-dihydroxy-3,3'-diisopropyl-5,5'-dipropylbiphenyl (1.1 g, 55.5%).

4,4'-dihydroxy-3,3'-diisopropyl-5,5'-dipropylbiphenyl: $^1$H NMR (300 MHz, CDCl$_3$) δ 7.50 (s, 4H), 5.35 (s, 2H), 2.65-2.62 (t, 8H), 1.66-1.63 (m, 8H), 0.92-0.89 (t, 12H).

EXAMPLE 8

Compound 9: 4'-hydroxy-3,3',5,5'-tetraisopropylbiphenyl-4-carboxylic acid

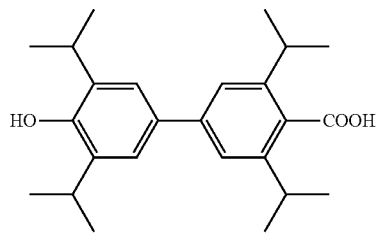 [SMILES: CC(C)c1cc(-c2cc(C(C)C)c(C(=O)O)c(C(C)C)c2)cc(C(C)C)c1O]

4,4'-dihydroxy-3,3',5,5'-tetraisopropylbiphenyl (10.00 g, 28.21 mmol) was dissolved in dichloromethane (50 mL), PBr₃ (15.27 g, 56.41 mmol) was added dropwise thereto in an ice bath, reacted at room temperature for 5 h, neutralized with sodium bicarbonate solution, and extracted with ethyl acetate to obtain 3.23 g yellow solid. The yellow solid was dissolved in anhydrous THF, n-butyllithium (0.99 g, 15.48 mmol) was added thereto at −78° C., and then charged with nitrogen for protection. A reaction was carried out by charging carbon dioxide below the liquid interface, followed by post-treatment to give 4'-hydroxy-3,3'5,5'-tetraisopropylbiphenyl-4-carboxylic acid (1.35 g, 45.61%).

4'-hydroxy-3,3'5,5'-tetraisopropylbiphenyl-4-carboxylic acid: $^1$H NMR (300 MHz, CDCl$_3$) δ 11.0 (s,1H), 7.89 (s,2H), 7.51 (s, 2H), 5.35 (s, 1H), 3.07-3.01 (m, 2H), 2.89-2.85 (m, 2H), 1.23-1.17 (m, 24H).

EXAMPLE 9

Compound 10: 4-chloro-4'-hydroxy-3,3',5,5'-tetraisopropylbiphenyl, and compound 11: 4,4'-dichloro-3,3',5,5'-tetraisopropylbiphenyl

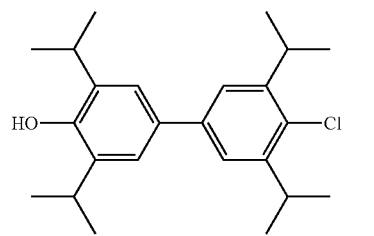

4-chloro-4'-hydroxy-3,3',5,5'-tetraisopropylbiphenyl

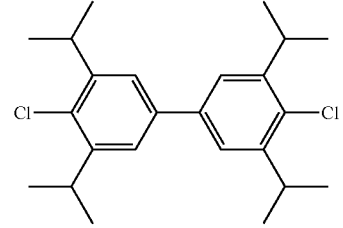

4,4'-dichloro-3,3',5,5'-tetraisopropylbiphenyl 4,4'-dihydroxy-3,3',5,5'-tetraisopropylbiphenyl (2 g, 5.64 mmol) was slowly added to phosphorus oxychloride (5 mL) at room temperature and refluxed for 1 h. the reaction mixture was slowly added dropwise to ice water and stirred continuously, extracted with ethyl acetate, dried over anhydrous sodium sulfate and filtered, and the filtrate was purified with petroleum ether-ethyl acetate eluent to give 4-chloro-4'-hydroxy-3,3',5,5'-tetraisopropylbiphenyl (500 mg, 23.76%) as a yellow solid and 4,4'-dichloro-3,3'5,5'-tetraisopropylbiphenyl (0.72 g, 32.61%) as a yellow solid.

4-chloro-4'-hydroxy-3,3',5,5'-tetraisopropylbiphenyl (500 mg, 23.76%) as a yellow solid; $^1$H NMR (300 MHz, CDCl$_3$) δ 7.28 (s, 2H), 7.20 (s, 2H), 4.88 (s, 1H), 3.47-3.40 (m, 2H), 3.27-3.20 (m,2H), 1.38-1.35 (d, 12H), 1.32-1.28 (t, 12H).

4,4'-dichloro-3,3'5,5'-tetraisopropylbiphenyl (0.72 g, 32.61%) as a yellow solid; $^1$H NMR (300 MHz, CDCl$_3$) δ 7.29 (s, 4H), 2.08 (s, 4H), 1.38-1.15 (m, 24H).

EXAMPLE 10

Compound 12: 4'-hydroxy-3,3',5,5'-tetraisopropylbiphenyl-4-carboxylate, and compound 13: 3,3',5,5'-tetraisopropylbiphenyl-4,4'-dicarboxylate

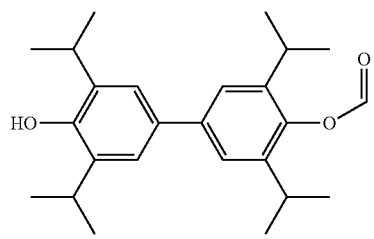

4'-hydroxy-3,3',5,5'-tetraisopropylbiphenyl-4-carboxylate

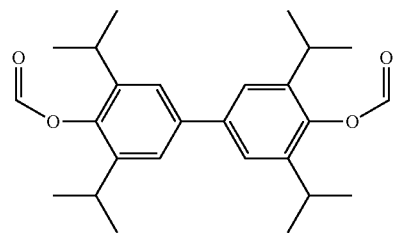

3,3',5,5'-tetraisopropylbiphenyl-4,4'-dicarboxylate

Under nitrogen protection, 3,3',5,5'-tetraisopropyl-4,4'-dihydroxybiphenyl (0.5 g, 2.7 mmol), 40 mL of formic acid and anhydrous aluminum chloride (3.0 g, 22.5 mmol) was added in a 100 mL round bottom flask and refluxed for 5 h. The reaction was terminated followed by addition of water, and then extracted with ethyl acetate. The organic phase was washed with saturated sodium bicarbonate and then with saturated brine, dried over anhydrous sodium sulfate and filtered, and the filtrate was purified with petroleum ether-ethyl acetate eluent to give 4'-hydroxy-3,3',5,5'-tetraisopropylbiphenyl-4-carboxylate (0.12 g, 20%) as a white solid; to give 3,3',5,5'-tetraisopropylbiphenyl-4,4'-dicarboxylate (0.3 g, 40%) as a white solid.

4'-hydroxy-3,3',5,5'-tetraisopropylbiphenyl-4-carboxylate: white solid; $^1$H NMR (300 MHz, CDCl$_3$) δ 9.6 (s, 1H), 7.65 (s, 2H), 7.51 (s, 2H), 3.07-3.02 (m, 4H), 1.26-1.23 (m, 24H).

3,3',5,5'-tetraisopropylbiphenyl-4,4'-dicarboxylate: white solid, $^1$H NMR (300 MHz, CDCl$_3$) δ 9.72 (s, 2H), 7.57 (s, 4H), 5.06-5.04 (d, 4H), 3.06-3.02 (m, 4H), 1.23-1.20 (d, 24H).

EXAMPLE 11

Compound 14: 4'-hydroxy-3,3',5,5'-tetraisopropylbiphenyl-2-amino-3-methylbutyrate

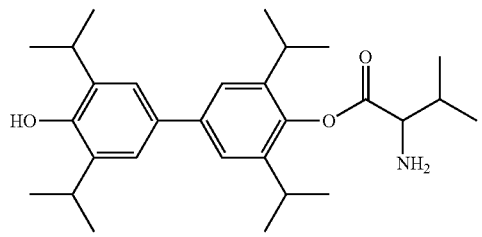 [SMILES: CC(C)c1cc(-c2cc(C(C)C)c(OC(=O)C(N)C(C)C)c(C(C)C)c2)cc(C(C)C)c1O]

3,3',5,5'-tetraisopropyl-4,4'-dihydroxybiphenyl (1 g, 2.8 mmol), Boc-valine (0.73 g, 3.36 mmol), phosphorus pentoxide (1.987 g, 14 mmol), and 30 mL dichloromethane were added in a 50 mL round bottom flask, and stirred at room temperature for 8 h. After the reaction was complete, 10 mL of water was added thereto and stirred for 1 h. An appropriate amount of ammonia was added, extracted with methylene chloride, washed with water and then with saturated sodium chloride, dried over anhydrous sodium sulfate, and purified by column chromatography to give a white solid (0.16 g, 13%).

White solid, 4'-hydroxy-3,3',5,5'-tetraisopropylbiphenyl-2-amino-3-methylbutyrate: $^1$H NMR (300 MHz, CDCl$_3$) δ 7.57 (s, 2H), 7.51 (s, 2H), 5.35 (s, 1H), 5.12-5.10 (d, 2H), 4.25-4.24 (d, 1H), 3.05-3.02 (m, 4H), 2.68-2.66 (m, 1H), 1.21-1.18 (d, 24H), 0.92-0.90 (d, 6H).

EXAMPLE 12

Compound 15: Ethyl 1-(4'-hydroxy-3,3',5,5'-tetraisopropylbiphenyl-4-oxo)acetate

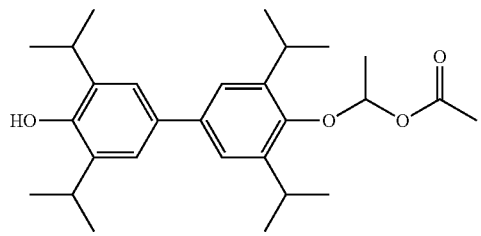 [SMILES: CC(=O)OC(C)Oc1c(C(C)C)cc(-c2cc(C(C)C)c(O)c(C(C)C)c2)cc1C(C)C]

3,3',5,5'-tetraisopropyl-4,4'-dihydroxybiphenyl (1 g, 2.8 mmol), ethyl chloroacetate (0.411 g, 3.36 mmol), sodium hydroxide (0.336 g, 8.4 mmol), and 60 mL of dichloromethane were sequentially added in a 100 mL round bottom flask, and stirred at room temperature for 8 h. After the reaction was complete, the reaction solution was filtered, extracted with dichloromethane, washed with saturated sodium chloride, dried over anhydrous sodium sulfate, and purified by column chromatography to give a white solid (0.12 g, 10%).

White solid, Ethyl 1-(4'-hydroxy-3,3',5,5'-tetraisopropylbiphenyl-4-oxo) acetate: $^1$H NMR (300 MHz, CDCl$_3$) δ 7.57 (s, 2H), 7.48 (s,2H), 5.25 (s, 1H), 3.01-2.98 (m, 4H), 2.21 (s, 3H), 1.82-1.80 (d, 3H), 1.16-1.14 (d, 24H).

EXAMPLE 13

Effects of Compound 1-15 on Neurological Impairment Score, Cerebral Infarct Volume, Fas, IL-1β, and TNF-α in Brain Tissues, and Cell Apoptosis in Rats with Cerebral Ischemic Reperfusion Injury (1) Material:

An aqueous solution of compound 1-15 in PEG400 at a concentration of 10 mg/mL, in which the concentration of PEG400 in the PEG400 aqueous solution was 400 mg/ml; GL-22M low temperature centrifuge (Hubei Saite Xiangyi); B12000 image analyzer (Chengdu Techman Software Co., Ltd.), SOD and MDA assay kits (Nanjing Jiancheng Bioengineering Research Institute); Fas and TUNEL kits (Wuhan Boside Biological Engineering Co., Ltd.), IL-1β and TNF-α kits (Shanghai HengYuan Biotechnology Co., Ltd.); other reagents were made in China, analytically pure.

(2) Method:

1. Experimental Animals and Grouping 336 healthy male SD rats weighing 250-300 g, provided by the Experimental Animal Center of the Fourth Military Medical University, were randomly divided into 14 groups: the sham operation group, the ischemic reperfusion group, and Examples 1-12 groups (i.e., the Example groups). The biphenyl derivatives used in Examples 1 to 12 are shown in Table 1:

TABLE 1

| Example groups | Biphenyl derivatives |
| --- | --- |
| Example 1 group | Compound 1 |
| Example 2 group | Compound 2 |
| Example 3 group | Compound 3 |
| Example 4 group | Compound 4 |
| Example 5 group | Compound 6 |
| Example 6 group | Compound 7 |
| Example 7 group | Compound 8 |
| Example 8 group | Compound 9 |
| Example 9 group | Compound 10 |
| Example 10 group | Compound 12 |
| Example 11 group | Compound 14 |
| Example 12 group | Compound 15 |

2. Animal Model Preparation and Treatment

Rats were intraperitoneally injected with 10% chloral hydrate 350 mg/kg after anesthesia and opened up at the center of the neck in accordance with the Zea Longa modified method. The right common carotid artery was separated, and the right external carotid artery branches was ligated. A small opening was made at the distal end of the external carotid artery, and a previously prepared thread was inserted through the common carotid artery and the external carotid artery bifurcation into the internal carotid artery, till the anterior end of the middle cerebral artery, with an immersed depth of 18 to 19 mm. The thread was then secured, and the wound was sutured layer by layer. After the operation, the rats were placed in a clean incubator to wake up. The criteria for a successfully prepared cerebral ischemia model was: after waking up, the rats showed Horner syndrome on the right side and hemiplegia on the left side. The sham operation group, the ischemic reperfusion group, and the Example groups were prepared strictly according to the requirements of the cerebral ischemic reperfusion model, while in the sham operation group the thread was put only into the external carotid artery. The animals were allowed to eat and drink freely after waking up. After 2 h, the thread was pulled out to achieve reperfusion. The sham operation group, the ischemic reperfusion group, and the Example groups were administered intravenously the aqueous solution of the biphenyl derivatives in PEG400 at 40 mg/kg (40 mg/kg means that 40 mg of the test compound per kg of the body weight of rats) 30 min before reperfusion and 12 h after reperfusion, respectively. The sham operation group and the ischemic reperfusion group were injected with the same amount of blank PEG400 aqueous solution at the same time point.

3. Neurological Impairment Score in Rats

The neurological impairment was scored in each group 24 h after reperfusion. The scoring was in accordance with the Longa 5-grade method: grade 0: no nerve injury symptom; grade 1: inability of stretching the contralateral forepaw; grade 2: circling to the opposite side; grade 3: tumbling to the opposite side; grade 4: no autonomous activity with loss of consciousness.

4. Sample Collection and Preparation 24 hours after reperfusion, 8 rats in each group were sacrificed by decapitation, the brain was removed, rinsed with PBS (pH 7.4) at $-20°$ i for 20 min, evenly sliced (with a thickness of 2 mm), stained in a 2% TTC solution at $37°\%$ in the dark for 30 min, fixed in 10% formalin for 24 h, and photographs were taken to analyze the infarct volume. A mixture of femoral arterial and venous blood was drawn from another 8 rats in each group under anesthesia, placed in a low temperature centrifuge at 4° C., centrifuged at 3500 r/min for 20 min, and the supernatant was stored in a refrigerator at $-20°$ C. ready for SOD and MDA detection. After the blood was drawn, a perfusion needle was insert through the apex to the ascending aorta, and saline at 4° C. was rapid infused until the effluent became clear, followed by 4% paraformaldehyde phosphate buffer perfusion for fixation; the brain was removed by craniotomy, and brain tissues 2 mm in front of and behind the optic chiasma were taken and fixed, dehydrated, rendered transparent, impregnated in wax, and embedded. Brain continuous coronary tissue pathological sections were consecutively cut for later use. The remaining 8 rats in each group were sacrificed, brains were removed, the ischemic brain hemispheres were immediately taken on an ice tray, and 10% brain tissue homogenate was prepared for the detection of IL-1β and TNF-α.

5. Determination of Relative Infarct Volume

The infarct area in each brain section was analyzed and quantified by the imageJ image software, and the ratio of cerebral infarction volume in the overall brain volume was calculated.

6. SOD and MDA Determination

SOD and MDA were determined strictly in accordance with instructions of the kit.

7. Fas Determination

The immunohistochemical method was used for determination. Brain tissue paraffin sections were dewaxed into water, washed with 3% $H_2O_2$ to eliminate endogenous peroxidase activity, and rinsed with distilled water for 3 times. Sodium citrate buffer was used for antigen heat repairing, and blocking with calf serum was carried out at room temperature for 15 min; a rabbit anti-mouse Fas antibody was added dropwise, allowed to stand at $4°t$ overnight, biotinylated goat anti-rabbit IgG was added dropwise, and heated in a water bath at $37°a$ for 20 min. Washing with PBS for 5 min was continuously repeated 4 times, followed by staining with DAB and sufficient washing without counterstaining. The sections were then gradient dehydrated with alcohol, made transparent with toluene, sealed and fixed. Images were captured by a video camera under high-power optical microscope and inputted into the image analysis system for image analysis. Five non-overlapping fields were randomly selected from each section. Five areas in each field were selected for determination of gray scale. The average gray scale was calculated, and the average gray scale was inversely proportional to the rate of positive expression.

8. Apoptosis Determination

The TUNEL method was used for determination. Brain tissue paraffin sections were dewaxed into water, washed with 3% $H_2O_2$ to eliminate endogenous peroxidase activity, and rinsed with distilled water for 2 min, repeated 3 times. A labelling solution was added for labelling at $37°t$ for 2 h, and a blocking solution was added for blocking at room temperature for 30 min. A biotinylated anti-digoxin antibody was added for a reaction at $37°a$ for 30 min, and SABC was added for a reaction at $37°a$ for 30 min. The sections were continuously rinsed with TBS for 5 min repeatedly for 4 times, stained with DAB, sufficiently washed, mild counterstained with Hematoxylin, gradient dehydrated with alcohol, made transparent with toluene, sealed and fixed. Five non-overlapping fields in semi-dark band were randomly selected from each section and inputted into the image analysis system. The number of apoptotic cells was counted, and the average was designated the number of apoptotic cells.

9. Determination of IL-1β and TNF-α

Brain tissue homogenate was hypothermally centrifuged at 3000 rpm for 15 min, the supernatant was taken, and IL-1β and TNF-α were determined in strict accordance with instructions of the kits.

(3) Results:

1. The biphenyl derivatives substantially improve the neurological impairment in the MCAO model rats, and the detailed scores according to the Longa scoring standard are shown in Table 2 below.

TABLE 2

| Groups | Average score of neurological impairment |
|---|---|
| Sham operation group | 0 |
| Ischemic reperfusion group | 3.2 |
| Example 1 group | 2.0 |
| Example 2 group | 2.1 |
| Example 3 group | 2.4 |
| Example 4 group | 2.2 |
| Example 5 group | 2.2 |
| Example 6 group | 2.0 |
| Example 7 group | 2.1 |
| Example 8 group | 2.3 |
| Example 9 group | 2.4 |
| Example 10 group | 2.2 |
| Example 11 group | 2.2 |
| Example 12 group | 2.4 |

2. The biphenyl derivatives can significantly reduce cerebral infarction volume in the MCAO model rats: except for the sham operation group having no visible infarction focus, the other groups had different degrees of infarction occurred. With Analysis and calculation with the imageJ software, detailed data is listed in Table 3.

TABLE 3

| Groups | Relative Brain infarction volume (%) |
|---|---|
| Sham operation group | 0 |
| Ischemic reperfusion group | 35.28 ± 5.22 |
| Example 1 group | 18.71 ± 4.69* |
| Example 2 group | 23.22 ± 3.12* |
| Example 3 group | 25.41 ± 3.59* |
| Example 4 group | 20.38 ± 4.92* |
| Example 5 group | 23.55 ± 5.67* |
| Example 6 group | 19.35 ± 4.02* |
| Example 7 group | 19.29 ± 3.54* |
| Example 8 group | 25.83 ± 2.38* |
| Example 9 group | 24.74 ± 6.13* |
| Example 10 group | 23.91 ± 5.44* |
| Example 11 group | 23.59 ± 4.11* |
| Example 12 group | 25.54 ± 3.29* |

Compared with the ischemic reperfusion group
*$p < 0.05$

3. The biphenyl derivatives can significantly reduce the consumption of endogenous oxygen free radical scavenger SOD, reduce the lipid peroxidation damage, and decrease the serum MDA content in the MCAO model rats: as compared with the sham operation group, the SOD activities of the other groups decreased, and the SOD activities of the Example groups were all higher than that of the ischemic reperfusion group; meanwhile, as compared with the sham operation group, the serum MDA contents of other groups increased, and the MDA contents of the Example group were all lower than that of the ischemic reperfusion group. Detailed data is listed in Table 4.

TABLE 4

| Groups | SOD ACTIVITY (U/mL) | MDA CONTENT (mmol/mL) |
|---|---|---|
| Sham operation group | 101.54 ± 3.45 | 2.49 ± 0.66 |
| Ischemic reperfusion group | 82.14 ± 4.37 | 7.22 ± 0.61 |
| Example 1 group | 96.78 ± 2.94* | 4.74 ± 0.67* |
| Example 2 group | 94.46 ± 2.19* | 5.44 ± 0.49* |
| Example 3 group | 93.15 ± 3.05* | 5.36 ± 0.47* |
| Example 4 group | 95.66 ± 3.18* | 4.68 ± 0.39* |
| Example 5 group | 95.01 ± 3.22* | 4.47 ± 0.34* |
| Example 6 group | 96.89 ± 3.49* | 4.26 ± 0.41* |
| Example 7 group | 94.51 ± 2.19* | 4.97 ± 0.50* |
| Example 8 group | 96.09 ± 3.33* | 5.12 ± 0.47* |
| Example 9 group | 92.26 ± 2.96* | 5.61 ± 0.71* |
| Example 10 group | 95.16 ± 3.88* | 4.89 ± .0.36* |
| Example 11 group | 96.71 ± 4.29* | 4.92 ± 0.52* |
| Example 12 group | 92.39 ± 5.27* | 5.37 ± 0.55* |

Compared with ischemic reperfusion group
*$p < 0.05$

4. The biphenyl derivatives can effectively down-regulate cellular Fas expression in brain tissues of the MCAO model rats: there were few Fas positive cellular expression in the sham operation group; the other groups had different degrees of expression in the cortical penumbra, and microscopic observation showed that the cell membrane and the cytoplasm in brown were Fas-positive cells. As compared with the sham operation group, the average gray scales of the other groups decreased, and the average gray scales of the Example groups were significantly higher than that of the ischemic reperfusion group. Detailed data was listed in Table 5.

TABLE 5

| Groups | Fas average gray scale |
|---|---|
| Sham operation group | 175.96 ± 5.14 |
| Ischemic reperfusion group | 134.33 ± 6.18 |
| Example 1 group | 162.47 ± 3.96* |
| Example 2 group | 148.36 ± 5.33* |
| Example 3 group | 144.56 ± 6.32* |
| Example 4 group | 159.68 ± 5.06* |
| Example 5 group | 148.02 ± 4.16* |
| Example 6 group | 155.33 ± 3.78* |
| Example 7 group | 157.26 ± 4.05* |
| Example 8 group | 148.82 ± 7.62* |
| Example 9 group | 147.11 ± 5.61* |
| Example 10 group | 145.06 ± 4.08* |
| Example 11 group | 152.12 ± 6.17* |
| Example 12 group | 144.26 ± 3.47* |

Compared with ischemic reperfusion group
*$p < 0.05$

5. The biphenyl derivatives can effectively inhibit brain cell apoptosis: there were few apoptotic cells in the sham operation group, while the other groups had different degrees of distribution in the cortical penumbra, and microscopic observation showed that those with brown granules in the nucleus were apoptotic cells. Compared with the sham group, the apoptotic cells were increased in the other groups, and were significantly less in the Example groups than in the ischemic reperfusion group. Detailed data was listed in Table 6.

TABLE 6

| Groups | Number of apoptotic cells |
|---|---|
| Sham operation group | 4.62 ± 1.54 |
| Ischemic reperfusion group | 37.26 ± 4.10 |
| Example 1 group | 19.14 ± 4.24* |
| Example 2 group | 24.65 ± 3.41* |
| Example 3 group | 25.14 ± 2.54* |
| Example 4 group | 21.49 ± 3.18* |
| Example 5 group | 20.56 ± 4.29* |
| Example 6 group | 19.47 ± 5.02* |
| Example 7 group | 20.28 ± 3.76* |
| Example 8 group | 24.81 ± 3.35* |
| Example 9 group | 25.47 ± 4.19* |
| Example 10 group | 22.18 ± 5.22* |
| Example 11 group | 24.19 ± 4.29* |
| Example 12 group | 26.27 ± 5.37* |

Compared with ischemic reperfusion group
*$p < 0.05$

6. The biphenyl derivatives can effectively down-regulate the cellular expression of IL-1β and TNF-α in brain tissues of the MCAO model rats: as compared with the sham operation group, the expression of IL-1β and TNF-α in the other groups significantly increased, wherein the expression of IL-1β and TNF-α in the Example groups were significantly lower than that in the ischemic reperfusion group. Detailed data was listed in Table 7.

TABLE 7

| Groups | IL-1β content (ng/mL) | TNF-α content (ng/mL) |
|---|---|---|
| Sham operation group | 0.39 ± 0.08 | 2.74 ± 0.21 |
| Ischemic reperfusion group | 0.92 ± 0.14 | 6.47 ± 0.65 |
| Example 1 group | 0.63 ± 0.12* | 4.11 ± 0.72* |
| Example 2 group | 0.79 ± 0.11* | 5.03 ± 0.59* |
| Example 3 group | 0.66 ± 0.05* | 4.26 ± 0.54* |
| Example 4 group | 0.68 ± 0.07* | 4.19 ± 0.36* |
| Example 5 group | 0.74 ± 0.09* | 5.01 ± 0.59* |
| Example 6 group | 0.64 ± 0.03* | 4.16 ± 0.44* |

TABLE 7-continued

| Groups | IL-1β content (ng/mL) | TNF-α content (ng/mL) |
|---|---|---|
| Example 7 group | 0.63 ± 0.08* | 4.32 ± 0.61* |
| Example 8 group | 0.64 ± 0.14* | 4.35 ± 0.46* |
| Example 9 group | 0.63 ± 0.07* | 5.02 ± 0.39* |
| Example 10 group | 0.67 ± 0.05* | 4.68 ± 0.61* |
| Example 11 group | 0.71 ± 0.07* | 5.31 ± 0.51* |
| Example 12 group | 0.74 ± 0.06* | 4.95 ± 0.67* |

Compared with ischemic reperfusion group
*p < 0.05

EXAMPLE 14

Effects of Compound 1-15 on Neurological Impairment Score, Cerebral Infarct Volume, Fas, IL-1β, and TNF-α in Brain Tissues, and Cell Apoptosis in Rats with Permanent Cerebral Ischemia Injury (1) Material:

An aqueous solution of compound 1-15 in PEG400 at a concentration of 10 mg/mL, in which the concentration of PEG400 in the PEG400 aqueous solution was 400 mg/ml; GL-22M low temperature centrifuge (Hubei Saite Xiangyi); BI2000 image analyzer (Chengdu Techman Software Co., Ltd.), SOD and MDA assay kits (Nanjing Jiancheng Bio-engineering Research Institute); Fas and TUNEL kits (Wuhan Boside Biological Engineering Co., Ltd.), IL-1β and TNF-α kits (Shanghai HengYuan Biotechnology Co., Ltd.); other reagents were made in China, analytically pure.

(2) Method:

1. Experimental Animals and Grouping 336 healthy male SD rats weighing 250-300 g, provided by the Experimental Animal Center of the Fourth Military Medical University, were randomly divided into 5 groups: the sham operation group, the permanent cerebral ischemia model group, and Examples 1-12 groups. The biphenyl derivatives used in each of the Examples 1-12 groups were the same as those in Example 13.

2. Animal Model Preparation and Treatment

Rats were intraperitoneally injected with 10% chloral hydrate 350 mg/kg after anesthesia and opened up at the center of the neck in accordance with the Zea Longa modified method. The right common carotid artery was separated, and the right external carotid artery branches was ligated. A small opening was made at the distal end of the external carotid artery, and a previously prepared thread was inserted through the common carotid artery and the external carotid artery bifurcation into the internal carotid artery, till the anterior end of the middle cerebral artery, with an immersed depth of 18 to 19 mm. The thread was then secured, and the wound was sutured layer by layer. After the operation, the rats were placed in a clean incubator to wake up. The criteria for a successfully prepared cerebral ischemia model was: after waking up, the rats showed Horner syndrome on the right side and hemiplegia on the left side. The sham operation group, the permanent cerebral ischemia model group, and the Example groups were prepared strictly according to the requirements of the cerebral ischemic reperfusion model, while in the sham operation group the thread was put only into the external carotid artery. The animals were allowed to eat and drink freely after waking up. The sham operation group, the permanent cerebral ischemia model group, and the Example groups were administered intravenously the aqueous solution of the biphenyl derivatives in PEG400 at 40 mg/kg (40 mg/kg means that 40 mg of the test compound per kg of the body weight of rats) 30 min before insertion of thread and 12 h after embolism, respectively. The sham operation group and the permanent cerebral ischemia model group were injected with the same amount of blank PEG400 aqueous solution at the same time point.

3. Neurological Impairment Score in Rats

The neurological impairment was scored in each group 24 h after the embolism. The scoring was in accordance with the Longa 5-grade method: grade 0: no nerve injury symptom; grade 1: inability of stretching the contralateral forepaw; grade 2: circling to the opposite side; grade 3: tumbling to the opposite side; grade 4: no autonomous activity with loss of consciousness.

4. Sample Collection and Preparation 24 hours after the embolism, 8 rats in each group were sacrificed by decapitation, the brain was removed, rinsed with PBS (pH 7.4) at −20°i for 20 min, evenly sliced (with a thickness of 2 mm), stained in a 2% TTC solution at 37°% in the dark for 30 min, fixed in 10% formalin for 24 h, and photographs were taken to analyze the infarct volume. A mixture of femoral arterial and venous blood was drawn from another 8 rats in each group under anesthesia, placed in a low temperature centrifuge at 4° C., centrifuged at 3500 r/min for 20 min, and the supernatant was stored in a refrigerator at −20° C. ready for SOD and MDA detection. After the blood was drawn, a perfusion needle was insert through the apex to the ascending aorta, and saline at 4° C. was rapid infused until the effluent became clear, followed by 4% paraformaldehyde phosphate buffer perfusion for fixation; the brain was removed by craniotomy, and brain tissues 2 mm in front of and behind the optic chiasma were taken and fixed, dehydrated, rendered transparent, impregnated in wax, and embedded. Brain continuous coronary tissue pathological sections were consecutively cut for later use. The remaining 8 rats in each group were sacrificed, brains were removed, the ischemic brain hemispheres were immediately taken on an ice tray, and 10% brain tissue homogenate was prepared for the detection of IL-1β and TNF-α.

5. Determination of Relative Infarct Volume

The infarct area in each brain section was analyzed and quantified by the imageJ image software, and the ratio of cerebral infarction volume in the overall brain volume was calculated.

6. SOD and MDA Determination

SOD and MDA were determined strictly in accordance with instructions of the kit.

7. Fas Determination

The immunohistochemical method was used for determination. Brain tissue paraffin sections were dewaxed into water, washed with 3% $H_2O_2$ to eliminate endogenous peroxidase activity, and rinsed with distilled water for 3 times. Sodium citrate buffer was used for antigen heat repairing, and blocking with calf serum was carried out at room temperature for 15 min; a rabbit anti-mouse Fas antibody was added dropwise, allowed to stand at 4°t overnight, biotinylated goat anti-rabbit IgG was added dropwise, and heated in a water bath at 37°a for 20 min. Washing with PBS for 5 min was continuously repeated 4 times, followed by staining with DAB and sufficient washing without counterstaining. The sections were then gradient dehydrated with alcohol, made transparent with toluene, sealed and fixed. Images were captured by a video camera under high-power optical microscope and inputted into the image analysis system for image analysis. Five non-overlapping fields were randomly selected from each section. Five areas in each field were selected for determination of gray scale. The average gray scale was calculated, and the average gray scale was inversely proportional to the rate of positive expression.

8. Apoptosis Determination

The TUNEL method was used for determination. Brain tissue paraffin sections were dewaxed into water, washed with 3% $H_2O_2$ to eliminate endogenous peroxidase activity, and rinsed with distilled water for 2 min, repeated 3 times. A labelling solution was added for labelling at 37°t for 2 h, and a blocking solution was added for blocking at room temperature for 30 min. A biotinylated anti-digoxin antibody was added for a reaction at 37°a for 30 min, and SABC was added for a reaction at 37°a for 30 min. The sections were continuously rinsed with TBS for 5 min repeatedly for 4 times, stained with DAB, sufficiently washed, mild counterstained with Hematoxylin, gradient dehydrated with alcohol, made transparent with toluene, sealed and fixed. Five non-overlapping fields in semi-dark band were randomly selected from each section and inputted into the image analysis system. The number of apoptotic cells was counted, and the average was designated the number of apoptotic cells.

9. Determination of IL-1β and TNF-α

Brain tissue homogenate was hypothermally centrifuged at 3000 rpm for 15 min, the supernatant was taken, and IL-1β and TNF-α were determined in strict accordance with instructions of the kits.

(3) Results:

1. The biphenyl derivatives can substantially improve the neurological impairment in permanent cerebral ischemia model rats, and the detailed scores according to the Longa scoring standard are shown in Table 8 below.

TABLE 8

| Groups | Average score of neurological impairment |
|---|---|
| Sham operation group | 0 |
| Permanent cerebral ischemia model group | 3.5 |
| Example 1 group | 2.4 |
| Example 2 group | 2.5 |
| Example 3 group | 2.8 |
| Example 4 group | 2.6 |
| Example 5 group | 2.4 |
| Example 6 group | 2.2 |
| Example 7 group | 2.3 |
| Example 8 group | 2.7 |
| Example 9 group | 2.8 |
| Example 10 group | 2.4 |
| Example 11 group | 2.3 |
| Example 12 group | 2.6 |

2. The biphenyl derivatives can significantly reduce cerebral infarction volume in the permanent cerebral ischemia model rats: except for the sham operation group having no visible infarction focus, the other groups had different degrees of infarction occurred. With Analysis and calculation with the imageJ software, detailed data is listed in Table 9.

TABLE 9

| Groups | Relative Brain infarction volume (%) |
|---|---|
| Sham operation group | 0 |
| Permanent cerebral ischemia model group | 39.82 ± 5.19 |
| Example 1 group | 24.71 ± 3.76* |
| Example 2 group | 27.92 ± 4.51* |
| Example 3 group | 29.76 ± 2.49* |
| Example 4 group | 25.83 ± 5.07* |
| Example 5 group | 28.37 ± 5.02* |
| Example 6 group | 22.53 ± 4.62* |
| Example 7 group | 21.39 ± 4.01* |
| Example 8 group | 29.74 ± 3.13* |
| Example 9 group | 30.11 ± 4.01* |
| Example 10 group | 26.46 ± 4.52* |
| Example 11 group | 28.98 ± 5.24* |
| Example 12 group | 31.79 ± 5.94* |

Compared with the permanent cerebral ischemia model group
*$p < 0.05$

3. The biphenyl derivatives can significantly reduce the consumption of endogenous oxygen free radical scavenger SOD, reduce the lipid peroxidation damage, and decrease the serum MDA content in the permanent cerebral ischemia model rats: as compared with the sham operation group, the SOD activities of the other groups decreased, and the SOD activities of the Example groups were all higher than that of the ischemic reperfusion group; meanwhile, as compared with the sham operation group, the serum MDA contents of other groups increased, and the MDA contents of the Example group were all lower than that of the ischemic reperfusion group. Detailed data is listed in Table 10.

TABLE 10

| Groups | SOD ACTIVITY (U/mL) | MDA CONTENT (mmol/mL) |
|---|---|---|
| Sham operation group | 102.29 ± 4.72 | 2.45 ± 0.67 |
| Permanent cerebral ischemia model group | 84.42 ± 3.88 | 7.05 ± 0.57 |
| Example 1 group | 97.36 ± 4.51* | 4.49 ± 0.59* |
| Example 2 group | 93.28 ± 3.49* | 5.10 ± 0.82* |
| Example 3 group | 93.61 ± 2.13* | 5.07 ± 0.77* |
| Example 4 group | 94.47 ± 3.81* | 4.79 ± 0.33* |
| Example 5 group | 95.31 ± 4.11* | 4.68 ± 0.42* |
| Example 6 group | 97.21 ± 4.36* | 4.31 ± 0.51* |
| Example 7 group | 98.28 ± 3.18* | 4.42 ± 0.39* |
| Example 8 group | 96.90 ± 3.69* | 5.06 ± 0.28* |
| Example 9 group | 93.62 ± 2.73* | 5.26 ± 0.49* |
| Example 10 group | 94.08 ± 2.83* | 4.95 ± .0.51* |
| Example 11 group | 95.76 ± 3.93* | 4.99. ± 0.45* |
| Example 12 group | 91.25 ± 3.84* | 6.03 ± 0.36* |

Compared with the permanent cerebral ischemia model group
*$p < 0.05$

4. The biphenyl derivatives can effectively down-regulate cellular Fas expression in brain tissues of the permanent cerebral ischemia model rats: there were few Fas positive cellular expression in the sham operation group; the other groups had different degrees of expression in the cortical penumbra, and microscopic observation showed that the cell membrane and the cytoplasm in brown were Fas-positive cells. As compared with the sham operation group, the average gray scales of the other groups decreased, and the average gray scales of the Example groups were significantly higher than that of the ischemic reperfusion group. Detailed data was listed in Table 11.

TABLE 11

| Groups | Fas average gray scale |
| --- | --- |
| Sham operation group | 178.69 ± 4.53 |
| Permanent cerebral ischemia model group | 126.7 ± 7.82 |
| Example 1 group | 158.28 ± 6.66* |
| Example 2 group | 149.63 ± 8.15* |
| Example 3 group | 143.39 ± 4.23* |
| Example 4 group | 156.53 ± 4.68* |
| Example 5 group | 143.02 ± 5.53* |
| Example 6 group | 151.63 ± 5.58* |
| Example 7 group | 153.46 ± 5.73* |
| Example 8 group | 145.24 ± 5.26* |
| Example 9 group | 144.31 ± 5.49* |
| Example 10 group | 140.62 ± 3.85* |
| Example 11 group | 150.72 ± 4.19* |
| Example 12 group | 139.48 ± 5.72* |

Compared with the permanent cerebral ischemia model group
*p < 0.05

5. The biphenyl derivatives can effectively inhibit brain cell apoptosis: there were few apoptotic cells in the sham operation group, while the other groups had different degrees of distribution in the cortical penumbra, and microscopic observation showed that those with brown granules in the nucleus were apoptotic cells. Compared with the sham group, the apoptotic cells were increased in the other groups, and were significantly less in the Example groups than in the ischemic reperfusion group. Detailed data was listed in Table 12.

TABLE 12

| Groups | Number of apoptotic cells |
| --- | --- |
| Sham operation group | 4.47 ± 1.09 |
| Permanent cerebral ischemia model group | 39.41 ± 4.34 |
| Example 1 group | 20.41 ± 5.02* |
| Example 2 group | 23.27 ± 3.78* |
| Example 3 group | 29.72 ± 3.43* |
| Example 4 group | 22.68 ± 5.50* |
| Example 5 group | 23.48 ± 3.62* |
| Example 6 group | 21.24 ± 5.30* |
| Example 7 group | 20.32 ± 4.19* |
| Example 8 group | 27.74 ± 4.20* |
| Example 9 group | 31.44 ± 5.19* |
| Example 10 group | 23.67 ± 5.13* |
| Example 11 group | 26.31 ± 3.86* |
| Example 12 group | 32.45 ± 4.21* |

Compared with the permanent cerebral ischemia model group
*p < 0.05

6. The biphenyl derivatives can effectively down-regulate the cellular expression of IL-1β and TNF-α in brain tissues of the permanent cerebral ischemia model rats: as compared with the sham operation group, the expression of IL-1β and TNF-α in the other groups significantly increased, wherein the expression of IL-1β and TNF-α in the Example groups were significantly lower than that in the ischemic reperfusion group. Detailed data was listed in Table 13.

TABLE 13

| Groups | IL-1β content (ng/mL) | TNF-α content (ng/mL) |
| --- | --- | --- |
| Sham operation group | 0.38 ± 0.05 | 2.58 ± 0.23 |
| Permanent cerebral ischemia model group | 0.95 ± 0.17 | 6.74 ± 0.47 |
| Example 1 group | 0.64 ± 0.09* | 4.25 ± 0.66* |
| Example 2 group | 0.78 ± 0.12* | 5.15 ± 0.88* |
| Example 3 group | 0.67 ± 0.08* | 4.45 ± 0.91* |
| Example 4 group | 0.71 ± 0.06* | 4.37 ± 0.62* |
| Example 5 group | 0.72 ± 0.11* | 5.23 ± 0.48* |
| Example 6 group | 0.55 ± 0.05* | 4.99 ± 0.53* |
| Example 7 group | 0.57 ± 0.08* | 4.26 ± 0.40* |
| Example 8 group | 0.65 ± 0.08* | 4.39 ± 0.73* |
| Example 9 group | 0.62 ± 0.12* | 5.17 ± 0.40* |
| Example 10 group | 0.66 ± 0.06* | 5.05 ± 0.54* |
| Example 11 group | 0.76 ± 0.04* | 5.16 ± 0.43* |
| Example 12 group | 0.75 ± 0.04* | 5.38 ± 0.59* |

Compared with the permanent cerebral ischemia model group
*p < 0.05.

EXAMPLE 15

Comparison of Efficacy of the Present Invention over Existing Positive Drugs

The therapeutic effects of propofol and edaravone respectively on the ischemic reperfusion model and the permanent cerebral ischemia model rats were evaluated according to the methods described above in Examples 13 and 14 (propofol 15 mg/kg; edaravone 3 mg/kg; herein, 15 mg/kg means that the rats were given 15 mg of propofol per kilogram of body weight, and 3 mg/kg means the rats were given 3 mg of edaravone per kilogram of body weight). Also, the change of behavior of the rats were observed after administration. The experimental results of the two models were shown in the following Table 14 and Table 15, respectively.

TABLE 14

Efficacy of positive drugs in ischemic reperfusion rat model

| | Model group | Example 1 group | Propofol injection (100 mg/10 mL) | Edaravone injection (30 mg/20 mL) |
| --- | --- | --- | --- | --- |
| Neurological impairment score | 3.2 | 2.0 | 2.5 | 2.6 |
| Relative brain infarction volume (%) | 35.28 ± 5.22 | 18.71 ± 4.69 | 27.14 ± 5.08* | 29.31 ± 3.95* |
| Fas average gray scale | 134.33 ± 6.18 | 162.47 ± 3.96 | 142.15 ± 5.71* | 139.65 ± 2.05* |
| SOD activity (U/mL) | 82.14 ± 4.37 | 96.78 ± 2.94 | 88.25 ± 2.19* | 88.16 ± 3.99* |
| MDA content (mmol/mL) | 7.22 ± 0.61 | 4.74 ± 0.67 | 5.58 ± 0.48* | 6.17 ± 0.54* |

TABLE 14-continued

Efficacy of positive drugs in ischemic reperfusion rat model

| | Model group | Example 1 group | Propofol injection (100 mg/10 mL) | Edaravone injection (30 mg/20 mL) |
|---|---|---|---|---|
| Number of apoptotic cells | 37.26 ± 4.10 | 19.14 ± 4.24 | 26.08 ± 3.72* | 28.6 ± 4.90* |
| IL-1β content (ng/mL) | 0.92 ± 0.14 | 0.63 ± 0.12 | 0.73 ± 0.09* | 0.75 ± 0.05* |
| TNF-α content (ng/mL) | 6.47 ± 0.65 | 4.11 ± 0.72 | 5.02 ± 0.31* | 5.14 ± 0.44* |
| Change of behavior of rats within 30 min after the administration 12 h after reperfusion | Sober, no significant difference as compared to pre-administration | Sober, no significant difference as compared to pre-administration | Anesthetized, loss of righting reflex | Sober, no significant difference as compared to pre-administration |

*Relative to Example 1, $p < 0.05$.

The results in Table 14 showed that the therapeutic effect of the biphenyl derivatives on the models was superior to that of the positive control drugs propofol and edaravone. Although most of the Examples show significant advantages over the efficacy of the positive drugs ($p<0.05$), Table 14 lists only the efficacy experimental results of Example 1 in comparison to the positive drugs as a reference. Further, it was found that the rats lost righting reflex after propofol administration and entered an anesthetic state while the rats in the other administration groups did not show obvious change of behavior.

TABLE 15

Positive drug efficacy in permanent cerebral ischemia model rats

| | Mode group | Example 1 group | Propofol injection (100 mg/10 mL) | Edaravone injection (30 mg/20 mL) |
|---|---|---|---|---|
| Neurological impairment score | 3.5 | 2.4 | 2.7 | 2.8 |
| Brain relative infarct volume (%) | 39.82 ± 5.19 | 24.71 ± 3.76 | 30.11 ± 3.58* | 31.29 ± 4.02* |
| Fas average gray value | 126.7 ± 7.82 | 158.28 ± 6.66 | 140.51 ± 4.84* | 138.95 ± 5.50* |
| SOD activity (U/mL) | 84.42 ± 3.88 | 97.36 ± 4.51 | 89.13 ± 3.82* | 90.62 ± 3.81* |
| MDA content (mmol/mL) | 7.05 ± 0.57 | 4.49 ± 0.59 | 6.10 ± 0.29* | 5.98 ± 0.44* |
| Number of apoptotic cells | 39.41 ± 4.34 | 20.41 ± 5.02 | 31.06 ± 3.55* | 33.19 ± 3.81* |
| IL-1β content (ng/mL) | 0.95 ± 0.17 | 0.64 ± 0.09 | 0.78 ± 0.07* | 0.76 ± 0.04* |
| TNF-α content ng/mL) | 6.74 ± 0.47 | 4.25 ± 0.66 | 5.40 ± 0.32* | 5.53 ± 0.54* |

*Relative to Example 1, $p < 0.05$.

The results in Table 15 showed that the therapeutic effect of the biphenyl derivatives on the models was superior to that of the positive control drugs propofol and edaravone. Although most of the Examples show significant advantages over the efficacy of the positive drugs ($p<0.05$), Table 15 lists only the efficacy experimental results of Example 1 in comparison to the positive drugs as a reference. Further, it was found that the rats lost righting reflex after propofol administration and entered an anesthetic state while the rats in the other administration groups did not show obvious change of behavior.

EXAMPLE 16

Oil-based Preparation

The formulation of the Oil-based preparation of the biphenyl derivative of the present invention can be as shown in Table 16:

TABLE 16

| Components | Amount in formulation | Components | Amount in formulation |
|---|---|---|---|
| 4'-hydroxy-3,3',5,5'-tetraisopropyl biphenyl-4-acetate | 200 mg | Benzyl Alcohol | 50 μl |
| Tetrahydrofuran polyglycol ether | 0.80 ml | Castor oil | Add to 1 ml |
| Vitamin E acetate | 5 mg | | |

EXAMPLE 17

Tablet

The formulation of the tablet of the biphenyl derivative of the present invention can be as shown in Table 17:

TABLE 17

| Components | Amount in formulation | Components | Amount in formulation |
|---|---|---|---|
| 4'-hydroxy-3,3',5,5'-tetraisopropyl biphenyl-2-amino-3-methylbutyrate | 200 mg | Starch pulp | 50 mg |
| lactose | 140 mg | Sodium carboxymethyl starch | 10 mg |
| Microcrystalline cellulose | 100 mg | Magnesium stearate | 1 mg |

EXAMPLE 18

Capsule

The formulation of the capsule of the biphenyl derivative of the present invention can be as shown in Table 18:

TABLE 18

| Components | Amount in formulation | Components | Amound in formulation |
|---|---|---|---|
| 4,4'-dihydroxy-3,3'-diisopropyl-5,5'-dipropylbiphenyl | 1 g | Egg yolk lecithin | 1.2 g |
| Olive oil | 10 g | Vitamin E | 0.2 g |

EXAMPLE 19

Emulsion

The formulation of the emulsion of the biphenyl derivative of the present invention can be as shown in Table 19:

TABLE 19

| Components | Amount in formulation | Components | Amound in formulation |
|---|---|---|---|
| [4-(4'-hydroxy-3,3',5,5'-tetraisopropyl) biphenyl)oxy]-4-carbonylbutyric acid | 1 g | Glycerin | 2.25 g |
| Soybean oil | 10 g | Sodium hydroxide | Appropriate amount |
| Egg yolk lecithin | 1.2 g | Water for Injection | Add to 100 ml |
| Vitamin E | 0.1 g | | |

The invention claimed is:

1. A biphenyl derivative represented by formula I or a pharmaceutically acceptable salt or solvate thereof,

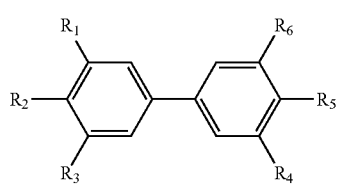

formula I wherein $R_1 R_3$, $R_4$, and $R_6$ in the biphenyl derivative are each independently n-propyl or isopropyl;

$R_2$ is selected from the group consisting of optionally substituted hydroxyl, optionally substituted carboxyl, optionally substituted acyl, optionally substituted ester, and halogen;

$R_5$ is selected from the group consisting of optionally substituted hydroxyl, optionally substituted carboxyl, optionally substituted acyl, optionally substituted ester, and halogen;

with the proviso that when $R_2$ and $R_5$ are both hydroxyl, $R_1$, $R_3$, $R_4$, and $R_6$ are not simultaneously isopropyl;

wherein the biphenyl derivative has a structure selected from a group consisting of:

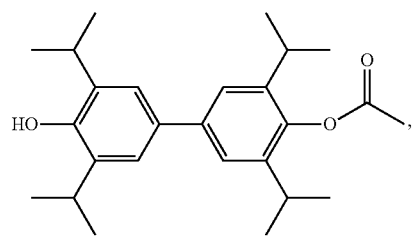

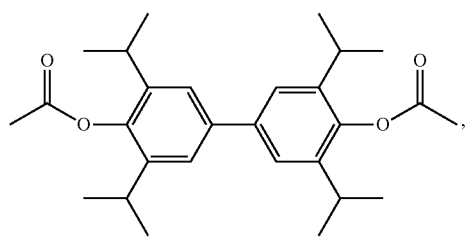

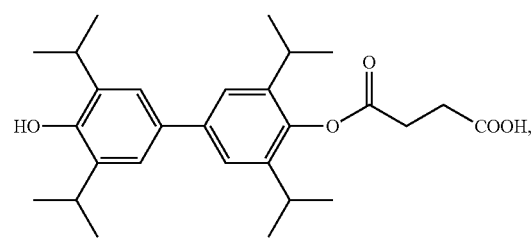

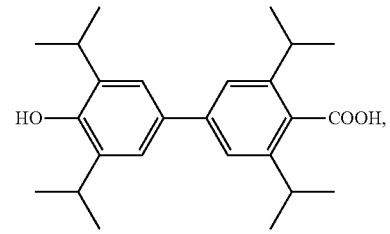

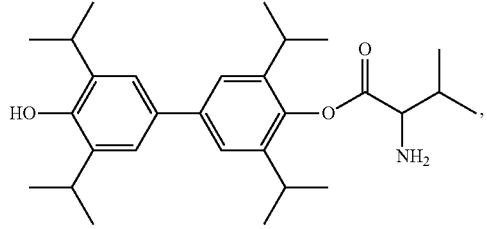

-continued

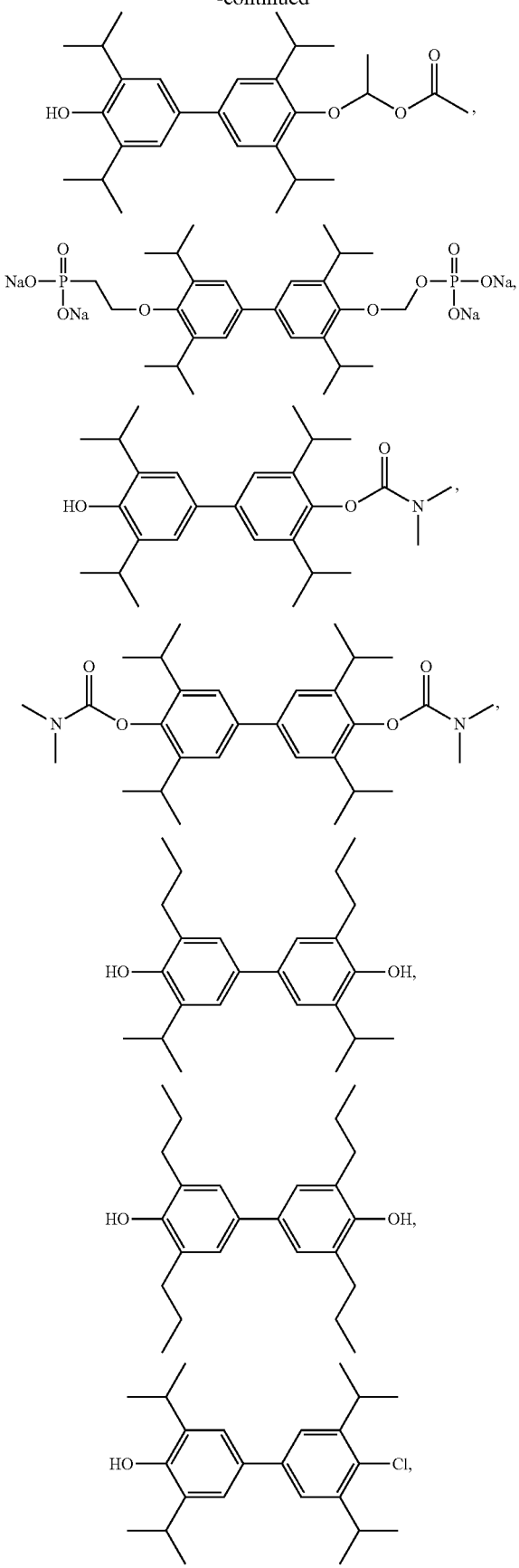

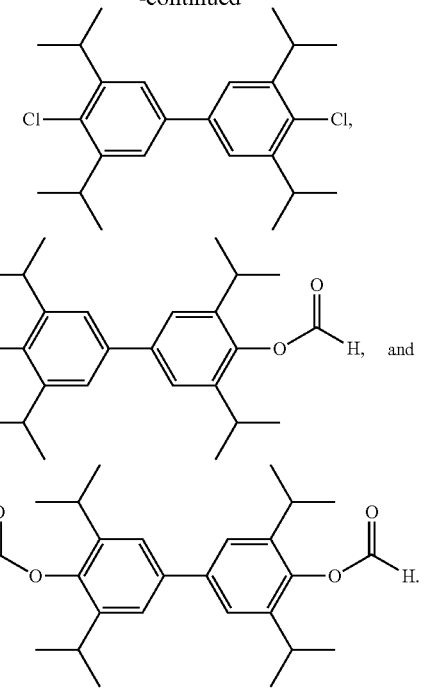

2. The biphenyl derivative or a pharmaceutically acceptable salt or solvate thereof according to claim 1, wherein $R_1$, $R_3$, $R_4$, and $R_6$ in the biphenyl derivative are each independently isopropyl.

3. The biphenyl derivative or a pharmaceutically acceptable salt or solvate thereof according to claim 1, wherein the pharmaceutically acceptable salt includes sulfate, phosphate, hydrochloride, hydrobromide, acetate, oxalate, citrate, succinate, gluconate, tartrate, p-toluenesulfonate, benzenesulfonate, methanesulfonate, benzoate, lactate, maleate, lithium salt, sodium salt, potassium salt, or calcium salt.

4. A pharmaceutical composition for the treatment and/or prevention of ischemic stroke, wherein the composition comprises the biphenyl derivative or a pharmaceutically acceptable salt or solvate thereof according to claim 1 and a pharmaceutical excipient.

5. The composition according to claim 4, wherein the pharmaceutical composition is in a pharmaceutically acceptable dosage form and the dosage form is selected from a tablet, a capsule, injection, emulsion, liposome, lyophilized powder or microsphere formulation.

6. A method of treating and/or preventing ischemic stroke in an animal or human, wherein the method comprises administering to the animal or human subject an effective dose of a biphenyl derivative or a pharmaceutically acceptable salt or solvate thereof according to claim 1.

7. The method according to claim 6, wherein the ischemic stroke includes damage caused by one or more of the following conditions: cerebral thrombosis, transient ischemic attack, basal ganglia infarction, atherosclerotic thrombotic cerebral infarction, lacunar infarction, cerebral embolism or brain vascular dementia.

8. The method according to claim 6, wherein the treatment and/or prevention of ischemic stroke in the animal or human is achieved by improving cerebral ischemia and/or reperfusion neurological impairment; reducing cerebral ischemia and/or reperfusion cerebral infarction volume; reducing the consumption of endogenous oxygen free radical scavenger SOD, reducing lipid peroxidation damage, and lowering the serum MDA content; down-regulating the cellular expression of Fas in brain tissues; inhibiting brain cell apoptosis or; down-regulating the cellular expression of IL-1β and TNF-α in brain tissues.

9. The biphenyl derivative or a pharmaceutically acceptable salt or solvate thereof according to claim 1, wherein the biphenyl derivative has a structure of:

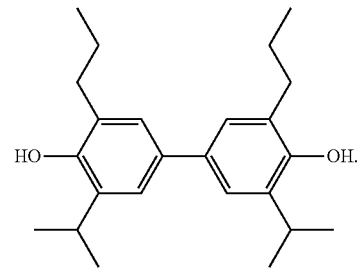 [SMILES: CCCc1cc(-c2cc(CCC)c(O)c(C(C)C)c2)cc(C(C)C)c1O]

10. The pharmaceutical composition according to claim 4, wherein the biphenyl derivative has a structure of:

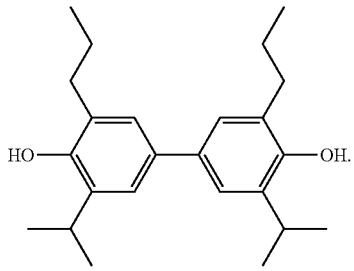

11. The method according to claim 6, wherein the biphenyl derivative has a structure of:

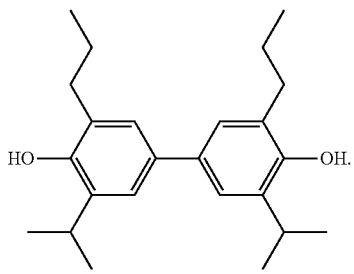 [SMILES: CCCc1cc(-c2cc(CCC)c(O)c(C(C)C)c2)cc(C(C)C)c1O]

12. The composition according to claim 4, wherein the capsule is a soft capsule.

* * * * *